US012691084B2

(12) United States Patent
Lee et al.

(10) Patent No.: US 12,691,084 B2
(45) Date of Patent: Jul. 28, 2026

(54) PHARMACEUTICAL COMPOSITION FOR PREVENTING OR TREATING BONE DISEASES

(71) Applicant: INDUSTRY FOUNDATION OF CHONNAM NATIONAL UNIVERSITY, Gwangju (KR)

(72) Inventors: Tae Hoon Lee, Gwangju (KR); Sun Woo Lee, Gwangju (KR); Eun Jin Cho, Gwangju (KR); Sang Hyun Min, Daegu (KR); Geun Joong Kim, Gwangju (KR); Dong Kyu Choi, Daegu (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 789 days.

(21) Appl. No.: 17/627,914

(22) PCT Filed: Jul. 13, 2020

(86) PCT No.: PCT/KR2020/009213
§ 371 (c)(1),
(2) Date: Jan. 18, 2022

(87) PCT Pub. No.: WO2021/010715
PCT Pub. Date: Jan. 21, 2021

(65) Prior Publication Data

US 2022/0313633 A1 Oct. 6, 2022

(30) Foreign Application Priority Data

Jul. 15, 2019 (KR) ........................ 10-2019-0084956

(51) Int. Cl.
*A61K 31/18* (2006.01)
*A61P 19/10* (2006.01)

(52) U.S. Cl.
CPC .............. *A61K 31/18* (2013.01); *A61P 19/10* (2018.01)

(58) Field of Classification Search
CPC .............................. A61K 31/18; C07C 311/08
See application file for complete search history.

(56) References Cited

U.S. PATENT DOCUMENTS

2009/0163545 A1* 6/2009 Goldfarb ................ A61K 31/13 514/688
2013/0331456 A1* 12/2013 Basu ....................... A61P 31/00 514/604

FOREIGN PATENT DOCUMENTS

KR 10-2013-0049672 A 5/2013
KR 10-1896415 B1 9/2018
KR 10-1902832 B1 10/2018
KR 10-1948917 B1 2/2019
KR 10-1992821 B1 6/2019
KR 10-2014200 B1 8/2019
WO WO 2014/144125 A1 9/2014
WO WO 2018-081378 A1 5/2018

OTHER PUBLICATIONS

Cho et al. (Molecules, 2019, 24(18), 3346, pp. 1-12).*
PubChem CID 11837035, downloaded Jul. 12, 2025, pp. 1-20, https://pubchem.ncbi.nlm.nih.gov/compound/11837035).*
PubChem 775 assay, downloaded Jul. 12, 2025, pp. 1-19, (https://pubchem.ncbi.nlm.nih.gov/bioassay/775).*
PubChem CID 11837035 (https:// https://pubchem.ncbi.nlm.nih.gov/compound/1295158, downloaded Jan. 3, 2026, pp. 1-20).*
European Search Report For EP20841290.8 issued on Jun. 22, 2023 from European patent office in a counterpart European patent application.
Jing Shan et al., "Identification of small 1-10 molecules for human hepatocyte expansion and iPS differentiation", Nature Chemical Biology, vol. 9, No. 8, pp. 514-520, 2013.
International Search Report for PCT/KR2020/009213 mailed on Nov. 6, 2020.

* cited by examiner

*Primary Examiner* — Susanna Moore
(74) *Attorney, Agent, or Firm* — The PL Law Group, PLLC

(57) ABSTRACT

A composition according to an embodiment of the present disclosure includes a N-phenyl-methylsulfonamido-acetamide compound represented by Formula 1, useful as a pharmaceutical compound to inhibit osteoclast differentiation and/or formation. The compound exhibits excellent prophylactic or therapeutic effects on various bone diseases including periodontitis and the like. Examples of the N-phenyl-methylsulfonamido-acetamide compound represented by Formula 1 are wherein the compound represented by Formula 1 above is selected from the group consisting of: 2-(N-(3-acetylphenyl)methylsulfonamido)-N-(2-(phenylthio)phenyl)acetamide; 2-(N-(5-chloro-2-methoxyphenyl)methylsulfonamido)-N-(2-(phenylthio)phenyl)acetamide; N-([1,1'-biphenyl]-2-yl)-2-(N-(3-acetylphenyl)methylsulfonamido)acetamide); 2-(N-(3-acetylphenyl)methylsulfonamido)-N-(2-(phenylamino)phenyl)acetamide; 2-(N-(3-acetylphenyl)methylsulfonamido)-N-(2-phenoxyphenyl)acetamide; and N2-(3,5-dimethylphenyl)-N2-(methylsulfonyl)-N-[2-(phenylthio)phenyl]alanineamide. A method for treating a bone disease caused by hyperdifferentiation of osteoclasts according to an embodiment of the present disclosure includes administering to a subject in need thereof the composition.

8 Claims, 13 Drawing Sheets

Specification includes a Sequence Listing.

A

B

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: NFATc1 Forward primer

<400> SEQUENCE: 1
cccgtcacat tctggtccat 20

<210> SEQ ID NO 2
<211> LENGTH: 23
<212> TYPE: DNA
<213> ORGANISM: Artificial Sequence
<220> FEATURE:
<223> OTHER INFORMATION: NFATc1 Reverse primer

<400> SEQUENCE: 2
caagtaaccg tgtagctcca caa 23

<210> SEQ ID NO 3
<211> LENGTH: 21
<212> TYPE: DNA
<213> ORGANISM: Artificial Sequence
<220> FEATURE:
<223> OTHER INFORMATION: CatK Forward primer

<400> SEQUENCE: 3
ggacgcagcg atgctaacta a 21

<210> SEQ ID NO 4
<211> LENGTH: 28
<212> TYPE: DNA
<213> ORGANISM: Artificial Sequence
<220> FEATURE:
<223> OTHER INFORMATION: CatK Reverse primer

<400> SEQUENCE: 4
cagagagaag ggaagtagag ttgtcact 28

<210> SEQ ID NO 5
<211> LENGTH: 21
<212> TYPE: DNA
<213> ORGANISM: Artificial Sequence
<220> FEATURE:
<223> OTHER INFORMATION: c-Fos Forward primer

<400> SEQUENCE: 5
cgaagggaac ggaataagat g 21

<210> SEQ ID NO 6
<211> LENGTH: 20
<212> TYPE: DNA
<213> ORGANISM: Artificial Sequence
<220> FEATURE:
<223> OTHER INFORMATION: c- Fos Reverse primer

<400> SEQUENCE: 6
gctgccaaaa taaactccag 20

<210> SEQ ID NO 7
<211> LENGTH: 20
<212> TYPE: DNA
<213> ORGANISM: Artificial Sequence
<220> FEATURE:
<223> OTHER INFORMATION: DC-STAMP Forward primer

<400> SEQUENCE: 7
gggagtcctg caccatatgg 20

<210> SEQ ID NO 8
<211> LENGTH: 22
<212> TYPE: DNA
<213> ORGANISM: Artificial Sequence
<220> FEATURE:
<223> OTHER INFORMATION: DC-STAMP Reverse primer

<400> SEQUENCE: 8
aggccagtgc tgactaggat ga 22

<210> SEQ ID NO 9
<211> LENGTH: 23
<212> TYPE: DNA
<213> ORGANISM: Artificial Sequence
<220> FEATURE:
<223> OTHER INFORMATION: OC-STAMP Forward primer

<400> SEQUENCE: 9
cagagtgacc acctgaacaa aca 23

<210> SEQ ID NO 10
<211> LENGTH: 20
<212> TYPE: DNA
<213> ORGANISM: Artificial Sequence
<220> FEATURE:
<223> OTHER INFORMATION: OC-STAMP Reverse primer

<400> SEQUENCE: 10
tgcctgaggt ccctgtgact 20

<210> SEQ ID NO 11
<211> LENGTH: 22
<212> TYPE: DNA
<213> ORGANISM: Artificial Sequence
<220> FEATURE:
<223> OTHER INFORMATION: TRAF6 Forward primer

<400> SEQUENCE: 11
aaagcgagag attctttccc tg 22

<210> SEQ ID NO 12
<211> LENGTH: 22
<212> TYPE: DNA
<213> ORGANISM: Artificial Sequence
<220> FEATURE:
<223> OTHER INFORMATION: TRAF6 Reverse primer

<400> SEQUENCE: 12
actggggaca attcactaga gc 22

<210> SEQ ID NO 13
<211> LENGTH: 19
<212> TYPE: DNA
<213> ORGANISM: Artificial Sequence
<220> FEATURE:
<223> OTHER INFORMATION: Acp5 Forward primer

<400> SEQUENCE: 13
cagctgtcct ggctcaaaa 19

-continued

<210> SEQ ID NO 14
<211> LENGTH: 20
<212> TYPE: DNA
<213> ORGANISM: Artificial Sequence
<220> FEATURE:
<223> OTHER INFORMATION: Acp5 Reverse primer

<400> SEQUENCE: 14
acatagccca caccgttctc 20

PHARMACEUTICAL COMPOSITION FOR PREVENTING OR TREATING BONE DISEASES

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2020/009213, filed Jul. 13, 2020, which claims priority to the benefit of Korean Patent Application No. 10-2019-0084956 filed in the Korean Intellectual Property Office on Jul. 15, 2019, the entire contents of which are incorporated herein by reference.

BACKGROUND

1. Technical Field

The present invention relates to a pharmaceutical composition and a health functional food for preventing or treating bone diseases.

2. Background Art

Bone tissue is a tissue in which bone resorption by osteoclasts and bone formation by osteoblasts are continuously maintained. Differentiation of osteoblasts is promoted by signal factors such as bone morphogenetic protein 2 (BMP2). On the other hand, differentiation of osteoclasts is promoted by receptor activator of nuclear factor kappa-β ligand (RANKL) signaling substances produced in the osteoblast differentiation stage, and apoptosis occurs when the differentiation is completed. Therefore, it is important to harmonize the differentiation and activity of the osteoblasts and osteoclasts during normal bone regeneration.

Periodontal inflammation is an inflammatory response by the defense of immune cells against apical bacterial infection. Neutrophils, which are mainly involved in periodontal inflammation, secrete prostaglandins as an inflammatory mediator. Cellular signaling substances such as prostaglandin and RANKL can activate osteoclasts that absorb bone tissue and cause resorption of alveolar bone around the inflamed area. For the treatment of chronic periodontitis, it is required to develop bone regeneration promoters or bone resorption inhibitors. In addition, in order to control abnormal bone resorption and restore normal bone regeneration processes, it is required to develop osteoclast differentiation inhibitors.

SUMMARY

An object of the present invention is to provide a pharmaceutical composition for preventing or treating bone diseases.

Another object of the present invention is to provide a health functional food for preventing or improving bone diseases.

1. A pharmaceutical composition for preventing or treating bone diseases caused by hyperdifferentiation of osteoclasts, the pharmaceutical composition including a compound represented by Formula 1 below or a pharmaceutically acceptable salt thereof:

[Formula 1]

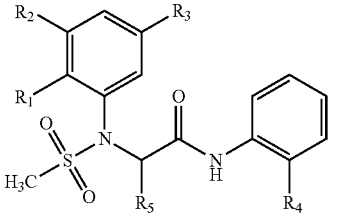

In Formula 1 above, $R_1$ is H or C1 to C3 alkoxy;

$R_2$ and $R_3$ are each independently H, C1 to C3 alkyl, C1 to C3 acyl or halo;

$R_4$ is phenyl, phenylthio, phenoxy or phenylamino; and $R_5$ is H or C1 to C3 alkyl.

2. The pharmaceutical composition according to the above 1, wherein $R_1$ is H or methoxy; $R_2$ and $R_3$ are each independently H, methyl, acetyl or chloro; and $R_5$ is H or methyl.

3. The pharmaceutical composition according to the above 1, wherein $R_1$ is C1 to C3 alkoxy, $R_3$ is halo, and $R_5$ is H; $R_1$, $R_3$ and $R_5$ are H, and $R_2$ is C1 to C3 acyl; or $R_1$ is H, and $R_2$, $R_3$ and $R_5$ are methyl.

4. The pharmaceutical composition according to the above 1, wherein the compound represented by Formula 1 above is selected from the group consisting of: 2-(N-(3-acetylphenyl)methylsulfonamido)-N-(2-(phenylthio)phenyl)acetamide; 2-(N-(5-chloro-2-methoxyphenyl)methylsulfonamido)-N-(2-(phenylthio)phenyl)acetamide; N-([1,1'-biphenyl]-2-yl)-2-(N-(3-acetylphenyl)methylsulfonamido) acetamide); 2-(N-(3-acetylphenyl)methylsulfonamido)-N-(2-(phenylamino)phenyl)acetamide; 2-(N-(3-acetylphenyl) methylsulfonamido)-N-(2-phenoxyphenyl)acetamide; and $N^2$-(3,5-dimethylphenyl)-$N^2$-(methylsulfonyl)-N-[2-(phenylthio)phenyl]alanineamide.

5. The pharmaceutical composition according to the above 1, wherein the bone disease is at least one selected from the group consisting of fracture, osteoporosis, rheumatoid arthritis, periodontitis, Paget's disease, osteomalacia, osteopenia, bone atrophy, osteoarthritis, and avascular femoral necrosis.

6. A health functional food for preventing or treating bone diseases caused by hyperdifferentiation of osteoclasts, the health functional food including a compound represented by Formula 1 below, or a food acceptable salt thereof:

[Formula 1]

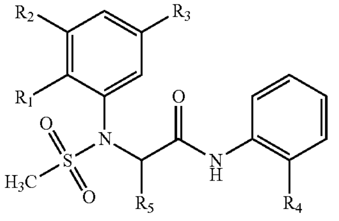

In Formula 1 above, $R_1$ is H or C1 to C3 alkoxy;

$R_2$ and $R_3$ are each independently H, C1 to C3 alkyl, C1 to C3 acyl or halo;

$R_4$ is phenyl, phenylthio, phenoxy or phenylamino; and $R_5$ is H or C1 to C3 alkyl.

7. The health functional food according to the above 6, wherein $R_1$ is H or methoxy; $R_2$ and $R_3$ are each independently H, methyl, acetyl or chloro; and $R_5$ is H or methyl.

8. The health functional food according to the above 6, wherein $R_1$ is C1 to C3 alkoxy, $R_3$ is halo, and $R_5$ is H; $R_1$, $R_3$ and $R_5$ are H, and $R_2$ is C1 to C3 acyl; or $R_1$ is H, and $R_2$, $R_3$ and $R_5$ are methyl.

9. The health functional food according to the above 6, wherein the compound represented by Formula 1 is selected from the group consisting of: 2-(N-(3-acetylphenyl)methylsulfonamido)-N-(2-(phenylthio)phenyl)acetamide; 2-(N-(5-chloro-2-methoxyphenyl)methylsulfonamido)-N-(2-(phenylthio)phenyl)acetamide; N-([1,1'-biphenyl]-2-yl)-2-(N-(3-acetylphenyl)methylsulfonamido)acetamide); 2-(N-(3-acetylphenyl)methylsulfonamido)-N-(2-(phenylamino) phenyl)acetamide; 2-(N-(3-acetylphenyl) methylsulfonamido)-N-(2-phenoxyphenyl)acetamide; and $N^2$-(3,5-dimethylphenyl)-$N^2$-(methylsulfonyl)-N-[2-(phenylthio)phenyl]alanineamide.

10. The health functional food according to the above 6, wherein the bone disease is at least one selected from the group consisting of fracture, osteoporosis, rheumatoid arthritis, periodontitis, Paget's disease, osteomalacia, osteopenia, bone atrophy, osteoarthritis, and avascular femoral necrosis.

The pharmaceutical composition of the present invention may inhibit differentiation and/or production of osteoclasts, thereby exhibiting excellent prophylactic or therapeutic effects for various bone diseases including periodontitis.

The health functional food of the present invention may inhibit differentiation and/or production of osteoclasts, thereby exhibiting excellent preventive or improvement effects for various bone diseases including periodontitis.

DETAILED DESCRIPTION

Figure 1:
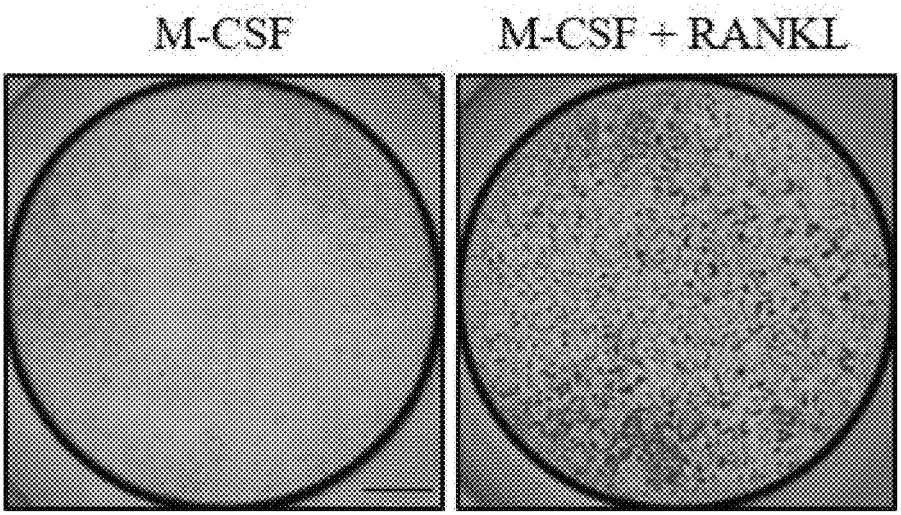
FIG. 1 shows results of confirming osteoclasts through TRAP staining by fixing cells on day 3 of differentiation from monocytes (M-CSF) into giant multinuclear cells by RANKL treatment (scale bar=1 mm).

Hereinafter, the present invention will be described in detail.

The present invention provides a pharmaceutical composition for preventing or treating bone diseases, which includes a compound represented by Formula 1 below or a pharmaceutically acceptable salt thereof:

[Formula 1]

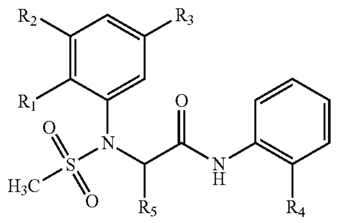

In Formula 1 above, $R_1$ is selected from the group consisting of H or C1 to C3 alkoxy;

$R_2$ and $R_3$ are each independently H, C1 to C3 alkyl, C1 to C3 acyl or halo;

$R_4$ is phenyl, phenylthio, phenoxy or phenylamino; and $R_5$ is H or C1 to C3 alkyl.

The term "alkyl" refers to a linear or branched saturated hydrocarbon group, such as methyl, ethyl, propyl, isopropyl, isobutyl, sec-butyl, tert-butyl, pentyl, hexyl, heptyl, octyl, nonyl, decyl, undecyl, tridecyl, pentadecyl and heptadecyl and the like. C1 to C10 alkyl means alkyl having 1 to 10 carbon atoms.

The term "alkoxy" refers to a group generated when a hydroxyl group of alcohol losses one hydrogen atom and can be represented by $C_nH_{2n+1}O^-$ (n is an integer of 1 or more). Alkoxy may be a linear or branched alkoxy group, and C1 to C3 alkoxy groups refer to each linear or branched alkoxy containing 1 to 3 carbon atoms. Representative examples of the alkoxy group may include methoxy, ethoxy, propoxy and isopropoxy groups. The term "hydroxyl group" means a functional group represented by —OH.

The term "acyl" refers to an alkylcarbonyl group containing an "alkyl" group bonded to a carbonyl group, a cycloalkylcarbonyl group containing a "cycloalkyl" group bonded to a carbonyl group, and an arylcarbonyl containing an "aryl" group bonded to a carbonyl group. For example, it may be acetyl, n-propanoyl, i-propanoyl, n-butyloyl, t-butyloyl, cyclopropanoyl, cyclobutanoyl, cyclopentanoyl, cyclohexanoyl, zoyl, α-naphtoyl or β-naphtoyl group. C1 to C3 acyl groups mean acyl groups containing 1 to 3 carbon atoms.

The term “halogen” or “halo” refers to a monovalent functional group of elements belonging to group 17 in the periodic table, and may include, for example, fluoro, chloro, bromo and iodo groups.

In Formula 1, $R_1$ may be selected from the group consisting of H and C1 to C3 alkoxy.

In Formula 1, $R_1$ may be H or methoxy.

In Formula 1, $R_2$ and $R_3$ may be each independently selected from the group consisting of H, C1 to C3 alkyl, C1 to C3 acyl and halo.

In Formula 1, $R_2$ and $R_3$ may be each independently selected from the group consisting of H, methyl, acetyl and chloro.

In Formula 1, $R_4$ may be selected from the group consisting of phenyl, phenylthio, phenoxy and phenylamino.

In Formula 1, $R_5$ may be selected from the group consisting of H and C1 to C3 alkyl.

In Formula 1, $R_5$ may be H or methyl.

In Formula 1, $R_1$ is C1 to C3 alkoxy, $R_2$ and $R_3$ are each H or halo, $R_4$ is selected from the group consisting of phenyl, phenylthio, phenoxy and phenylamino, and $R_5$ may be H or C1 to C3 alkyl.

According to an embodiment, in Formula 1, $R_1$ is methoxy, $R_2$ is H, $R_3$ is chloro, $R_4$ is phenylthio, and $R_5$ may be H or C1 to C3 alkyl.

In Formula 1, $R_1$ and $R_3$ are each H or halo, $R_2$ is C1 to C3 acyl, $R_4$ is selected from the group consisting of phenyl, phenylthio, phenoxy and phenylamino, and $R_5$ may be H or C1 to C3 alkyl.

According to an embodiment, in Formula 1, $R_1$ is H, $R_2$ is acetyl, $R_3$ is H, $R_4$ is selected from the group consisting of phenyl, phenylthio, phenoxy and phenylamino, and $R_5$ may be H.

In Formula 1, $R_1$ is H or halo, $R_2$ and $R_3$ are each independently C1 to C3 alkyl, $R_4$ is selected from the group consisting of phenyl, phenylthio, phenoxy and phenylamino, and $R_5$ may be H or C1 to C3 alkyl.

According to an embodiment, in Formula 1, $R_1$ is H, $R_2$ is methyl, $R_3$ is methyl, $R_4$ is selected from the group consisting of phenyl, phenylthio, phenoxy and phenylamino, and $R_5$ may be methyl.

The compound represented by Formula 1 may be selected from the group consisting of: 2-(N-(3-acetylphenyl)methylsulfonamido)-N-(2-(phenylthio)phenyl)acetamide; 2-(N-(5-chloro-2-methoxyphenyl)methylsulfonamido)-N-(2-(phenylthio)phenyl)acetamide; N-([1,1'-biphenyl]-2-yl)-2-(N-(3-acetylphenyl)methylsulfonamido)acetamide; 2-(N-(3-acetylphenyl)methylsulfonamido)-N-(2-(phenylamino) phenyl)acetamide; 2-(N-(3-acetylphenyl) methylsulfonamido)-N-(2-(phenoxyphenyl)acetamide; and $N^2$-(3,5-dimethylphenyl)-$N^2$-(methylsulfonyl)-N-[2-(phenylthio)phenyl]alanineamide.

The compound represented by Formula 1 may be selected from the group consisting of compounds represented by Formulae 2 to 7 below:

[Formula 2]

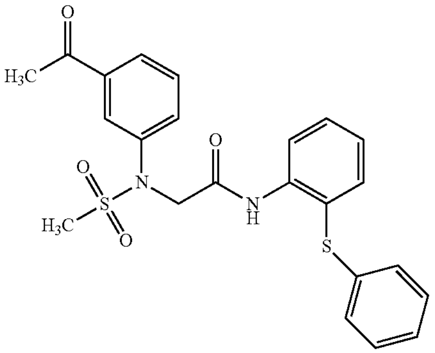

[Formula 3]

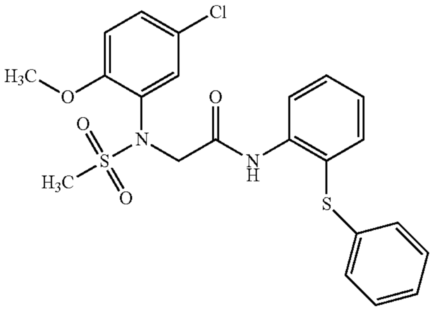

[Formula 4]

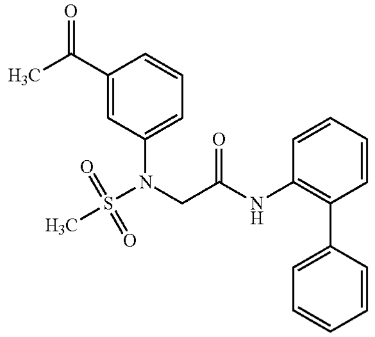

[Formula 5]

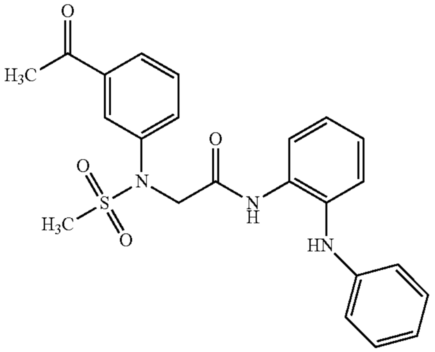

-continued

[Formula 6]

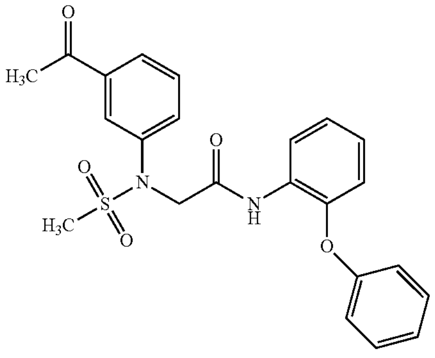

[Formula 7]

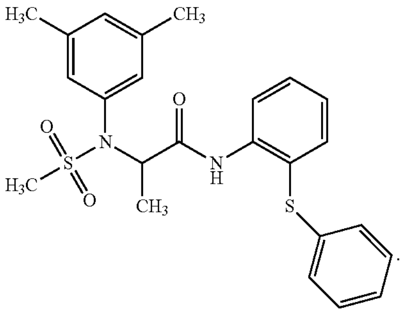

According to an embodiment, it is possible to provide a pharmaceutical composition for preventing or treating bone diseases, which includes each of compounds represented by Formulae 2 to 7, or a pharmaceutically acceptable salt thereof.

The term "pharmaceutically acceptable" refers to a feature that does not cause serious irritation to an individual, cells, tissues, etc. to which a compound or composition is administered, and does not impair biological activity and physical properties of the compound.

Pharmaceutically acceptable salts may be, for example, acid addition salts, base addition salts or metal salts.

The acid addition salts may be formed from inorganic acids such as hydrochloric acid, nitric acid, phosphoric acid, sulfuric acid, hydrobromic acid, hydroiodic acid, nitrous or phosphorous acid, aliphatic mono and dicarboxylates, phenyl-substituted alkanoates, hydroxy alkanoates and alkane dioates, and non-toxic organic acids such as aromatic acids, aliphatic and aromatic sulfonic acids. These pharmaceutically non-toxic salts may include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propyolate, oxalate, malonate, succinate, suberate, sebacate, fumarate, maleate, butine-1,4-dioate, nucleic acid-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, β_hydroxybutyrate, glycolate, malate, tartrate, methane sulfonate, propane sulfonate, naphthalene-1-sulfonate, naphthalene-2-sulfonate or mandelate. For example, the acid addition salt of the compound represented by Formula 1 may be obtained by dissolving the compound in an excess amount of aqueous acid solution and precipitating the salt using a hydrated organic solvent such as methanol, ethanol, acetone or acetonitrile.

The metal salt may be a sodium, potassium or calcium salt. The metal salt may be prepared using a base, for example, alkali-metal or alkaline earth metal salts may be obtained by dissolving the compound in an excess amount of alkali-metal hydroxide or alkaline earth metal hydroxide solution, filtering the non-dissolved compound salt, and evaporating and/or drying the filtrate.

The compound represented by Formula 1 and a pharmaceutically acceptable salt thereof may exhibit osteoclast differentiation inhibitory effects.

The compound represented by each of Formulae 2 to 7, and a pharmaceutically acceptable salt thereof, may exhibit osteoclast differentiation inhibitory effects.

The term "prevention" refers to any action that inhibits or delays bone disease.

The term "treatment" refers to any action that improves or beneficially alters symptoms of an individual suspected of and developed bone disease.

The compounds represented by Formulae 1 to 7 included in the composition of the present invention may be derived from nature or may be synthesized using a known chemical synthesis method.

Bone diseases that can be prevented or treated by the pharmaceutical composition of the present invention may be caused by an imbalance of activities between osteoblasts and osteoclasts.

Since bone is a living tissue, old bone is destroyed regularly and undergoes a reformation process to create new bones. In this process, osteoclasts destroy old and unnecessary bone tissues, and calcium is released into the blood stream to help maintain body functions, while osteoblasts play a role of regenerating the destroyed bone. This reaction continues 24 hours a day, and about 10% to 30% of adult bones are regenerated in this way every year. Therefore, the balance between the osteoclasts and the osteoblasts is very important, and this balance is regulated by various hormones and other body chemicals.

Specifically, the bone disease may be caused by osteoclast hyperdifferentiation or decrease in osteoblast activity, and specifically, the bone disease may be caused by osteoclast hyperdifferentiation.

When the osteoclasts are hyperdifferentiated, the osteoclasts may be increased abnormally and cause excessive bone resorption, thereby resulting in lower bone density. For example, various diseases such as osteoporosis, osteomalacia, osteopenia, bone atrophy, and periodontitis may be developed.

The bone diseases may include, for example, fracture, osteoporosis, rheumatoid arthritis, periodontitis, Paget's disease, osteomalacia, osteopenia, bone atrophy, osteoarthritis or avascular femoral necrosis, bone defects, fracture osteoporotic fractures, diabetic fractures, nonunion fractures, bone insufficiency, osteoporotic fracture, bone dysplasia, degenerative bone disease, malunion, bone union disorder, arthrosis, bone necrosis, osteoarthritis, bone tumor, bone cancer, etc., but it is not limited thereto. Preferably, the bone disease may be fracture, osteoporosis, rheumatoid arthritis, periodontitis, Paget's disease, osteomalacia, osteopenia, bone atrophy, osteoarthritis or avascular femoral necrosis, but it is not limited thereto.

Periodontitis is an inflammatory reaction caused by the defense of immune cells against apical bacterial infection. Neutrophils, which are mainly involved in periodontitis, secrete prostaglandins as an inflammatory mediator. The osteoclasts absorbing bone tissues are activated by cellular signaling substances such as prostaglandin, and the alveolar bone loss is observed around the inflamed area. Further, chronic periodontitis shows persistent inflammation in the apical region of the periodontal bone and erosion of the alveolar bone. If periodontitis becomes worsen and teeth cannot be saved, tooth extraction and implantation are performed. In order to prevent such conditions as described above, antibiotics should be administered to reduce the number of cells causing infection and osteoclast inhibitors are further administered to overcome the activation of osteoclasts by inflammatory mediators in the early stages of periodontitis, whereby alleviation and treatment of chronic periodontitis may be expected.

The pharmaceutical composition for preventing or treating bone diseases of the present invention may be used for the prevention or treatment of periodontitis based on bone resorption inhibitory effects.

The pharmaceutical composition of the present invention may be admixed and provided with known bone disease treatment substances.

The pharmaceutical composition of the present invention may be administered in combination with known substances for preventing or treating bone diseases.

The term "administration" refers to introducing a predetermined substance to an individual by an appropriate method, and the term "subject" refers to all animals such as rats, mice, livestock, as well as humans who have or may develop bone disease. As a specific example, it may be a mammal including a human.

If necessary, the pharmaceutical composition of the present invention may additionally include a known anti-bone disease compound.

Examples of these anti-bone disease compounds may include, for example, cinchonin, extracts of brown mealworm, aloe-emodin and omega-3 fatty acids, arteannnuin B, indole-2-carboxylate derivatives, euphrobia factor L1, scalcapflavon derivatives, and praxinelone, etc., but it is not limited thereto.

The pharmaceutical composition of the present invention may be in the form of a capsule, tablet, granule, injection, ointment, powder or beverage.

The pharmaceutical composition of the present invention may be formulated and used in oral dosage forms such as powder remedies, granules, capsules, tablets, and aqueous suspensions, external preparations, suppositories and injections.

The pharmaceutical composition of the present invention may contain an active ingredient alone, or may further include one or more pharmaceutically acceptable carriers, excipients, or diluents.

The pharmaceutical composition of the present invention may include a pharmaceutically acceptable carrier. The pharmaceutically acceptable carrier may be binders, lubricants, disintegrants, excipients, solubilizers, dispersants, stabilizers, suspending agents, coloring agents, flavoring agents, etc. for oral administration. Further, for injections, a buffering agent, a preservative, a soothing agent, a solubilizing agent, an isotonic agent, a stabilizer, etc. may be mixed and used. Further, for topical administration, a base agent, an excipient, a lubricant, a preservative, etc. may be used.

The formulation of the pharmaceutical composition of the present invention may be prepared in various ways by mixing the composition with the pharmaceutically acceptable carrier. For example, when administered orally, it may be prepared in the forms of tablets, troches, capsules, elixir, suspension, syrup, wafers, etc. Further, in the case of an injection, it may be prepared in a unit dosage ampoule or a multiple dosage form. In addition, the formulation of the pharmaceutical composition of the present invention may be prepared as a solution, suspension, tablet, capsule, sustained release formulation, or the like.

The carriers, excipients and diluents for formulation may include, for example, lactose, dextrose, sucrose, sorbitol, mannitol, xylitol, erythritol, malditol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, mineral oil, filler, anti-coagulant, lubricant, wetting agent, fragrance, emulsifier or preservative.

The administration route of the pharmaceutical composition of the present invention may include, for example oral, intravenous, intramuscular, intraarterial, intramedullary, intrathecal, intracardiac, transdermal, subcutaneous, intraperitoneal, intranasal, intestinal, topical, sublingual or rectal, but it is not limited thereto.

The pharmaceutical composition of the present invention may be administered orally or parenterally and, when administered parenterally, external preparations or injection methods such as intraperitoneal, rectal, subcutaneous, intravenous, intramuscular or intrathoracic injection may be selected.

The dosage of the pharmaceutical composition of the present invention may vary depending on the condition and weight of the patient, the degree of the disease, the form of the drug, the route and duration of administration, but may be appropriately selected by those skilled in the art.

For example, the pharmaceutical composition of the present invention may be administered at 0.0001 to 1000 mg/kg or 0.001 to 500 mg/kg per day. Further, the pharmaceutical composition of the present invention may be administered once a day, or may be divided several times. The administration dosage does not limit the scope of the present invention in any way.

In addition, the present invention provides a health functional food for preventing or improving bone diseases, which includes a compound represented by Formula 1, or a food acceptable salt thereof:

[Formula 1]

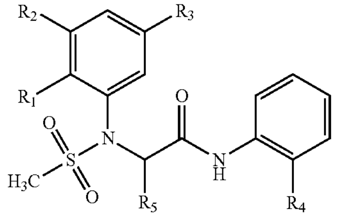

In Formula 1 above, $R_1$ is selected from the group consisting of H or C1 to C3 alkoxy;

$R_2$ and $R_3$ are each independently H, C1 to C3 alkyl, C1 to C3 acyl or halo;

$R_4$ is phenyl, phenylthio, phenoxy or phenylamino; and $R_5$ is H or C1 to C3 alkyl.

According to an embodiment, it is possible to provide a health functional food for preventing or improving bone disease, which includes a compound represented by each of Formulae 2 to 4, or a food acceptable salt thereof.

Since the compounds represented by Formulae 1 to 7 and the bone diseases have been described above, therefore will not be described in detail.

The health functional food of the present invention may be formulated as one selected from the group consisting of tablets, pills, powder remedies, granules, powders, capsules, and liquid formulations by further adding at least one of carriers, diluents, excipients and additives thereto.

The health functional food may be, for example, various foods, powders, granules, tablets, capsules, syrup, beverages, gums, teas, vitamin complexes, or health functional foods.

Additives that can be included in health functional foods may be selected from the group consisting of natural carbohydrates, flavoring agents, nutrients, vitamins, minerals (electrolytes), flavoring agents (synthetic flavors, natural flavors, etc.), coloring agents, fillers (cheese, chocolate, etc.), pectic acid or salts thereof, alginic acid and salts thereof, organic acids, protective colloidal thickeners, pH adjusters, stabilizers, preservatives, antioxidants, glycerin, alcohols, carbonation agents and pulp.

Examples of natural carbohydrates may be: monosaccharides such as glucose, fructose, and the like; disaccharides such as maltose, sucrose, and the like; and polysaccharides, for example, common sugars such as dextrin and cyclodextrin, and sugar alcohols such as xylitol, sorbitol, and erythritol and the like. Further, as the flavoring agent, natural flavors (taumatin, stevia extract (e.g., rebaudioside A, glycyrrhizin, etc.)), and synthetic flavors (saccharin, aspartame, etc.) may be advantageously used.

The health functional food may further include various nutrients, vitamins, minerals (electrolytes), flavoring agents such as synthetic flavors and natural flavors, coloring agents and thickeners (cheese, chocolate, etc.), pectic acid and salts thereof, alginic acid and salts thereof, and organic acids, protective colloidal thickeners, pH adjusters, stabilizers, preservatives, glycerin, alcohol, carbonation agents used in carbonated beverages, and pulp for production of natural fruit juices and vegetable beverages and the like.

The carriers, excipients, diluents and additives are not limited thereto, but may be selected from the group consisting of lactose, dextrose, sucrose, sorbitol, mannitol, erythritol, starch, gum acacia, calcium phosphate, alginate, gelatin, calcium phosphate, calcium silicate, microcrystalline cellulose, polyvinylpyrrolidone, cellulose, polyvinylpyrrolidone, methylcellulose, water, sugar syrup, methylcellulose, methyl hydroxy benzoate, propylhydroxy benzoate, talc, magnesium stearate and mineral oil.

When formulating the health functional food of the present invention, it may be prepared using diluents or excipients such as fillers, extenders, binders, wetting agents, disintegrants, and surfactants.

Hereinafter, the present invention will be more specifically described by way of the following preparative examples and examples.

In the following preparative examples and examples, PMSA-3-Ac (#25) is a compound represented by Formula 2 above; PMSA-2-OMe-5-Cl (#25-D12) (ChemBridge Corp. ID 7795298) is a compound represented by Formula 3 above; PMSA-Ph (#25-C) is a compound represented by Formula 4 above; PMSA-PhN (#25-N) is a compound represented by Formula 5 above; PMSA-PhO (#25-O) is a compound represented by Formula 6 above; and PSTP-3,5-Me (#25-D5) (ChemBridge Corp. ID 7973197) is a compound represented by Formula 7 above. In the present specification, the compounds represented by Formulae 1 to 7 may also be expressed as PMSA (N-phenyl-methylsulfonamide-acetamide) compounds.

PREPARATIVE EXAMPLES

Preparative Example 1. Preparation of PMSA-3-Ac (#25)

PMSA-3-Ac (#25) was prepared through the following steps.

1) Step 1: Preparation of methyl (3-acetylphenyl)glycinate (4)

[Scheme 1]

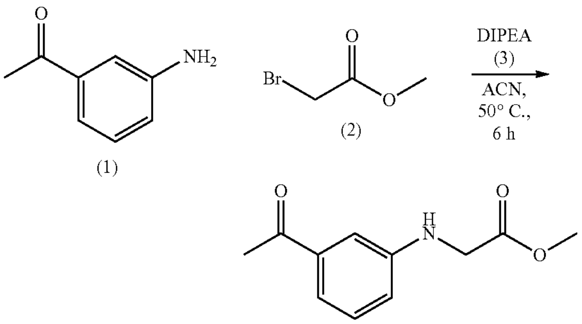

(1) (2) (4) 90%

To a 50 mL round bottom flask equipped with a stopper to which 1-(3-aminophenyl)ethan-1-one (1) (7.39 mmol, 1.0 equiv) was added, N,N-diisopropylethylamine dissolved in 10 mL of acetonitrile (3) (DIEPA) (11.08 mmol, 1.5 equiv) and methyl-2-bromoacetate (2) were slowly added. The solution was stirred at 50° C. for 6 hours with a condenser. After the reaction was completed, acetonitrile was removed by vacuum distillation at 50° C. After completely removing acetonitrile, EtOAc (30 mL) and water (20 mL) were charged and used for washing. EtoAc was collected. After repeating the above process twice, the organic layer was collected and removed by vacuum distillation at 50° C. After completely removing the organic layer in a vacuum state, 10 mL of EtOAc:n-Hexane was added in a 50:50 ratio, followed by stirring for 15 minutes. The precipitate was filtered to obtain methyl (3-acetylphenyl)glycinate (4) (yield: 90%, 1.379 g), which would be used in the next step without column purification.

2) Step 2: Preparation of methyl N-(3-acetylphenyl)-N-(methylsulfonyl)glycinate (7)

[Scheme 2]

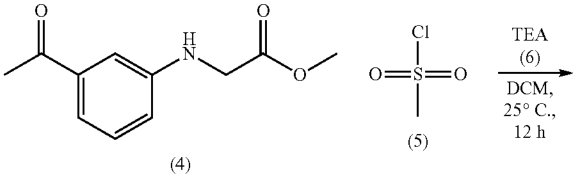

(4) (5)

-continued

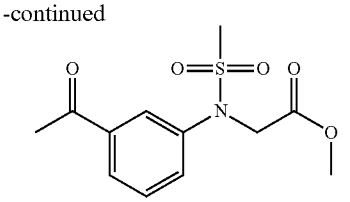

(7)
65%

To a 50 mL round bottom flask equipped with a stopper to which methyl (3-acetylphenyl) glycinate (4) (4.8 mmol, 1.0 equiv) as added, dichloromethane (DCM) (15 mL) and triethylamine (6) (TEA) (5.76 mmol, 1.2 equiv) were further added. After 15 minutes, methanesulfonyl chloride (5) (12 mmol, 2.5 equiv) was slowly added and stirring was continued at room temperature for 12 hours. The resulting reaction mixture was diluted with DCM (10 mL and washed with water (10 mL×2). The organic layer was collected and evaporated at 40° C. using a rotor vacuum. The mixture was purified through silica gel column chromatography (eluent: n-hexane/EtOAc=1:1), thereby obtaining methyl N-(3-acetylphenyl)-N-(methylsulfonyl)glycinate (7) (yield: 65%, 1.0725 g).

3) Step 3: Preparation of 3 N-(3-acetylphenyl)-N-(methylsulfonyl)glycine (10)

[Scheme 3]

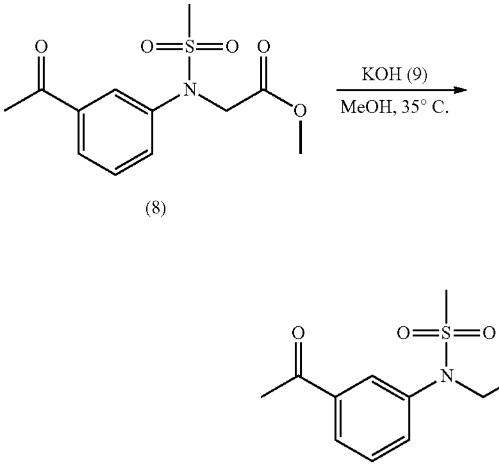

(8)

(10) 72%

Potassium hydroxide (KOH) (9) (6.62 mmol, 2.0 equiv) and ethanol (10 mL) were added to a 20 ml screw-cap vial, followed by stirring at room temperature until a clear solution was obtained. Thereafter, methyl N-(3-acetylphenyl)-N-(methylsulfonyl)glycerate (8) (3.1 mmol, 1 equiv) was added. The solution was heated at 35)(2 and stirred for 1 hour. Water (10 mL) and $Et_2O$ (10 ml) were added to the reaction mixture. The organic layer was collected and evaporated using a rotor vacuum at 40° C. to obtain a pale orange precipitate of 3 N-(3-acetylphenyl)-N-(methylsulfonyl)glycine (10) (yield: 72%, 0.616 g).

4) Step 4: PMSA-3-Ac Preparation

[Scheme 4]

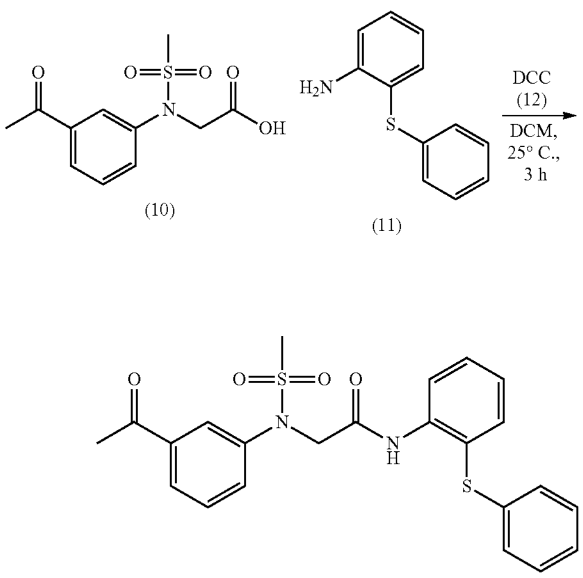

(10)

(11)

(13)

To a 5 mL screw-cap vial to which 2-(phenylthio)aniline (11) (0.43 mmol, 1.2 equiv) and N,N'-dicyclohexylcarbodiimide (DCC) in $CH_2Cl_2$ (2 mL) (12) (0.54 mmol, 1.5 equiv), N-(3-acetylphenyl)-N-(methylsulfonyl)glycine (10) (0.36 mmol, 1 equiv) was further added, followed by stirring at room temperature for 2 hours. The reaction mixture was filtered. The organic solvent in the filtrate was evaporated, and the mixture was purified through silica gel column chromatography (eluent: n-hexane/EtOAc=4/6), thereby obtaining 2-(N-(3-acetylphenyl)methylsulfonamido)-N-(2-(phenylthio)phenyl)acetamide (13) (yield: 40%, 0.03 g). The obtained. PMSA-3-Ac has a molecular weight of 454.56 g/mol, and $^1H$ NMR and $^{13}C$ NMR values are as follows.

$^1H$ NMR (500 MHz, $CDCl_3$) δ 9.10 (s, 1H), 8.44 (d, J=8.2 Hz, 1H), 8.05 (t, J=1.8 Hz, 1H), 7.86 (dt, 1H), 7.58-7.53 (m, 2H), 7.44-7.41 (m, 1H), 7.35 (t, J=7.9 Hz, 1H), 7.23-7.20 (m, 2H), 7.16-7.12 (m, 2H), 7.09-7.07 (m, 2H), 4.44 (s, 2H), 3.00 (s, 2H), 2.57 (s, 3H).

$^{13}C$ NMR (126 MHz, $CDCl_3$) δ 196.75 (s), 166.00 (s), 140.16 (s), 139.09 (s), 138.55 (s), 136.73 (s) 135.57 (s), 132.73 (s), 130.91 (s), 130.03 (s), 129.37 (s), 128.21 (s), 127.46 (s), 126.57 (s), 126.40 (s), 125.17 (s), 120.83 (s), 120.74 (a), 55.10 (s), 38.06 (s), 26.69 (s).

Preparative Example 2. Preparation of PMSA-Ph (#25-C)

The product was synthesized in the same manner as in Preparative Example 1 except that, instead of 2-(phenylthio) aniline (11) (0.43 mmol, 1.2 equiv) in Step 4 of Preparative Example 1, [1,1'-biphenyl]-2-amine (18) (0.43 mmol, 1.2 equiv) was used to carry out the reaction, thereby obtaining N-([1,1'-biphenyl]-2-yl)-2-(N-(3-acetylphenyl)methyl sulfonamide)acetamide) (19) (yield: 70%, 0.064 g). A specific reaction scheme is shown in Scheme 5 below.

[Scheme 5]

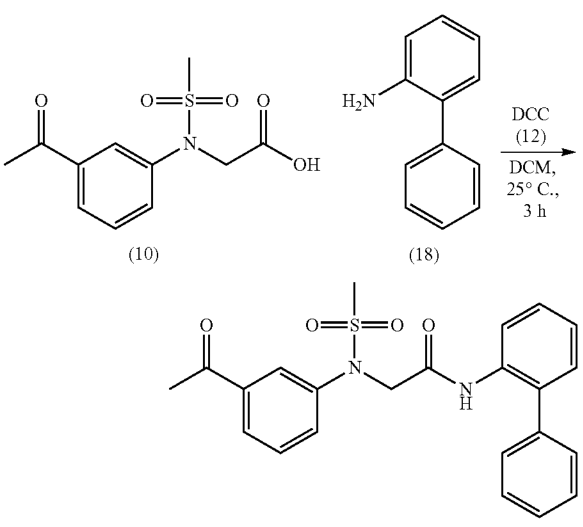

(10) (18)

(19)

The obtained PMSA-Ph (#25-C) has a molecular weight of 422.499 g/mol, and $^{1}H$ NMR and $^{13}C$ NMR values are as follows.

$^{1}H$ NMR (500 MHz, $CDCl_3$) δ 8.36 (d, J=8.3 Hz, 2H), 8.20 (s, 2H), 7.89-7.80 (m, 4H), 7.57 (t, J=7.5 Hz, 4H), 7.49 (dd, J=13.8, 6.6 Hz, 2H), 7.45-7.35 (m, 8H), 7.27 (dd, J=7.6, 1.4 Hz, 3H), 7.20 (t, J=7.4 Hz, 2H), 7.08 (d, J=6.8 Hz, 2H), 4.38 (s, 4H), 2.95 (s, 6H), 2.57 (s, 6H).

$^{13}C$ NMR (126 MHz, $CDCl_3$) δ 196.68 (s), 165.55 (s), 140.17 (s), 138.57 (s), 137.73 (s), 133.94 (s), 132.53 (s), 132.32 (s), 130.27 (s), 130.00 (s), 129.59 (s), 129.28 (s), 128.47 (s), 128.22 (d, J=4.5 Hz), 125.98 (s), 124.75 (s), 120.70 (s), 54.99 (s), 37.55 (s), 26.71 (s).

Preparative Example 3. Preparation of PMSA-PhN (#25-N)

The product was synthesized in the same manner as in Preparative Example 1 except that, instead of 2-(phenylthio) aniline (11) (0.43 mmol, 1.2 equiv) in Step 4 of Preparative Example 1, N'-phenylbenzene-1,2-diamine (16) (0.43 mmol, 1.2 equiv) was used to carry out the reaction, thereby obtaining 2-(N-(3-acetylphenyl)methylsulfonamido)-N-(2-(phenylamino)phenyl)acetamide (17). (yield: 55%, 0.051 g).

A specific reaction scheme is shown in Scheme 6 below.

[Scheme 6]

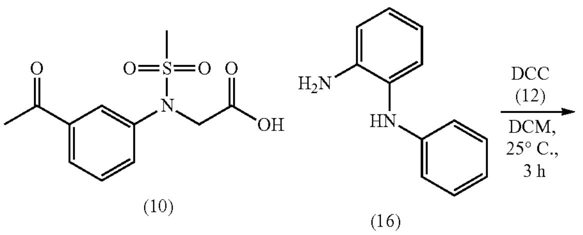

(10) (16)

-continued

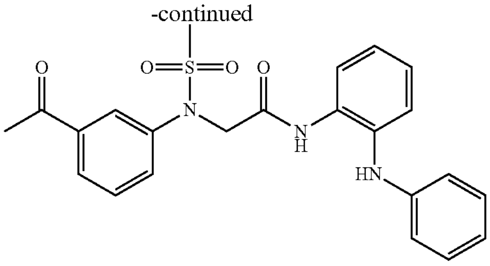

(17)

The obtained PMSA-PhN (#25-N) has a molecular weight of 437.514 g/mol, and $^{1}H$ NMR and $^{13}C$ NMR values are follows.

$^{1}H$ NMR (500 MHz, $CDCl_3$) δ 8.60 (s, 2H), 8.05-8.02 (m, 2H), 7.98 (dd, J=5.9, 3.6 Hz, 2H), 7.86 (d, J=7.8 Hz, 2H), 7.53 (dc, J=8.0, 1.3 Hz, 2H), 7.38 (t, J=7.9 Hz, 2H), 7.30-7.26 (m, 3H), 7.21 (dd, J=8.3, 7.6 Hz, 4H), 7.17-7.11 (m, 4H), 6.88 (t, J=7.4 Hz, 2H), 6.80 (d, J=7.7 Hz, 4H), 4.47 (s, 4H), 2.97 (s, 3H), 2.56 (s, 3H).

$^{13}C$ NMR (126 MHz, $CDCl_3$) δ 196.94 (s), 166.40 (s), 144.81 (s), 140.38 (s), 138.56 (s), 133.71 (s), 132.56 (s), 131.35 (s), 130.14 (s), 129.17 (s), 128.24 (s), 126.52 (s), 125.99 (s), 124.91 (s), 123.91 (s), 122.45 (s), 120.45 (s), 116.25 (s), 55.16 (s), 38.11 (s), 26.65 (s).

Preparative Example 4. Preparation of PMSA-PhO (#25-O)

The product was synthesized in the same manner as in Preparative Example 1 except that, instead of 2-(phenylthio) aniline (11) (0.43 mmol, 1.2 equiv) in Step 4 of Preparative Example 1, 2-phenoxyaniline (14) (0.43 mmol, 1.2 equiv) was used to carry out the reaction, thereby obtaining 2-(N-(3-acetylphenyl)methylsulfonamido)-N-(2-phenoxyphenyl) acetamide (15) (yield: 62%, 0.059 g). A specific reaction scheme is shown in Scheme 7 below.

[Scheme 7]

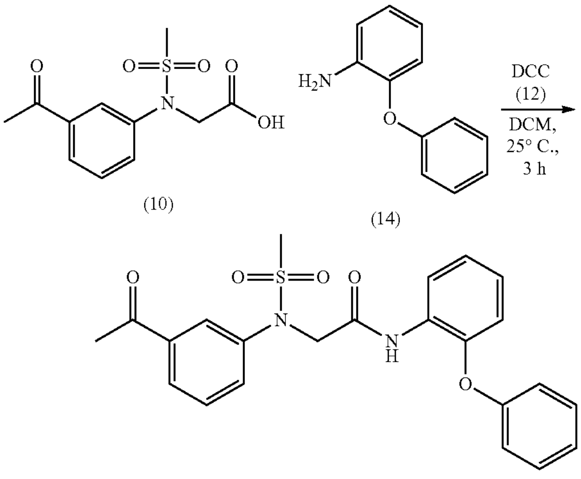

(10) (14)

(15)

The obtained PMSA-PhO (#25-O) has a molecular weight of 438.498 g/mol, and $^{1}H$ NMR and $^{13}C$ NMR values are as follows.

$^1H$ NMR (500 MHz, $CDCl_3$) δ 8.56 (s, 1H), 8.39 (dd, J=8.1, 1.1 Hz, 1H), 8.04 (t, J=1.8 Hz, 1H), 7.94-7.78 (m, 1H), 7.68-7.51 (m, 1H), 7.43-7.31 (m, 3H), 7.22-7.14 (m, 1H), 7.11 (td, J=7.9, 1.3 Hz, 1H), 7.08-7.00 (m, 3H), 6.86 (dd, J=8.1, 1.3 Hz, 1H), 4.54 (s, 2H), 3.04 (s, 3H), 2.54 (s, 3H).

$^{13}C$ NMR (126 MHz, $CDCl_3$) δ 196.78 (s), 165.78 (s), 156.15 (s), 145.92 (s), 140.16 (s), 140.16 (s), 138.61 (s), 132.71 (s), 130.07 (s), 128.79 (s), 128.22 (s), 126.59 (s), 124.71 (s), 124.13 (s), 123.93 (s), 120.77 (s), 118.77 (s), 117.68 (s), 55.14 (s), 38.31 (s), 26.61 (s).

Confirmation of Osteoclast Differentiation Inhibitory Effects

1. Inhibitory Effects of the Compound Represented by Formulae 2 to 6 on Osteoclast Differentiation Macrophages were isolated from bone marrow of 8-week old C57BL/6J mice, and seeded on a 96-well plate in an amount of $1\times10^4$ cells per well, followed by treating the cells with osteoclast differentiation factors M-CSF and RANKL at 30 ng/ml and 50 ng/ml, respectively. At the same time, the compounds were used for treatment, followed by culturing the cells for 3 to 4 days. Thereafter, differentiation influence was evaluated through TRAP staining and cell counting. Specific experimental procedures and results are as follows.

1) Isolation of Mouse Bone Marrow Cells and Differentiation of Osteoclasts

The bone marrow of a 10-week-old female mouse was isolated from the hip bone, femur and tibia, and incubated in α-MEM medium (Gibco, 12561-056, 10% fetal bovine serum, 1% penicillin/streptomycin) containing macrophage colony stimulating factor (M-CSF, PeproTech, 315-02, 30 ng/ml) for days so as to isolate only monocytes. The isolated monocytes were treated with receptor activator of nuclear factor kappa B ligand (RANKL, PeproTech, 315-11, 50 ng/ml) to induce osteoclast differentiation. When a morphology of fused multinuclear cells began to appear from day 3 after treatment with RANKL, the cells were differentiated into giant multinuclear cells for 4 to 6 days (see FIG. 1), and dead by cell apoptosis after 6 days. FIG. 1 shows results of confirming osteoclasts through TRAP staining, wherein the cells were fixed on day 3 when the monocytes (M-CSF) were differentiated into giant multinuclear cells by RANKL treatment (scale bar=1 mm).

During RANKL treatment, each PMSA compound was also used for treatment, followed by culturing the cells for 3 or 5 days to confirm the effects of inhibiting osteoclast differentiation.

Figure 2:
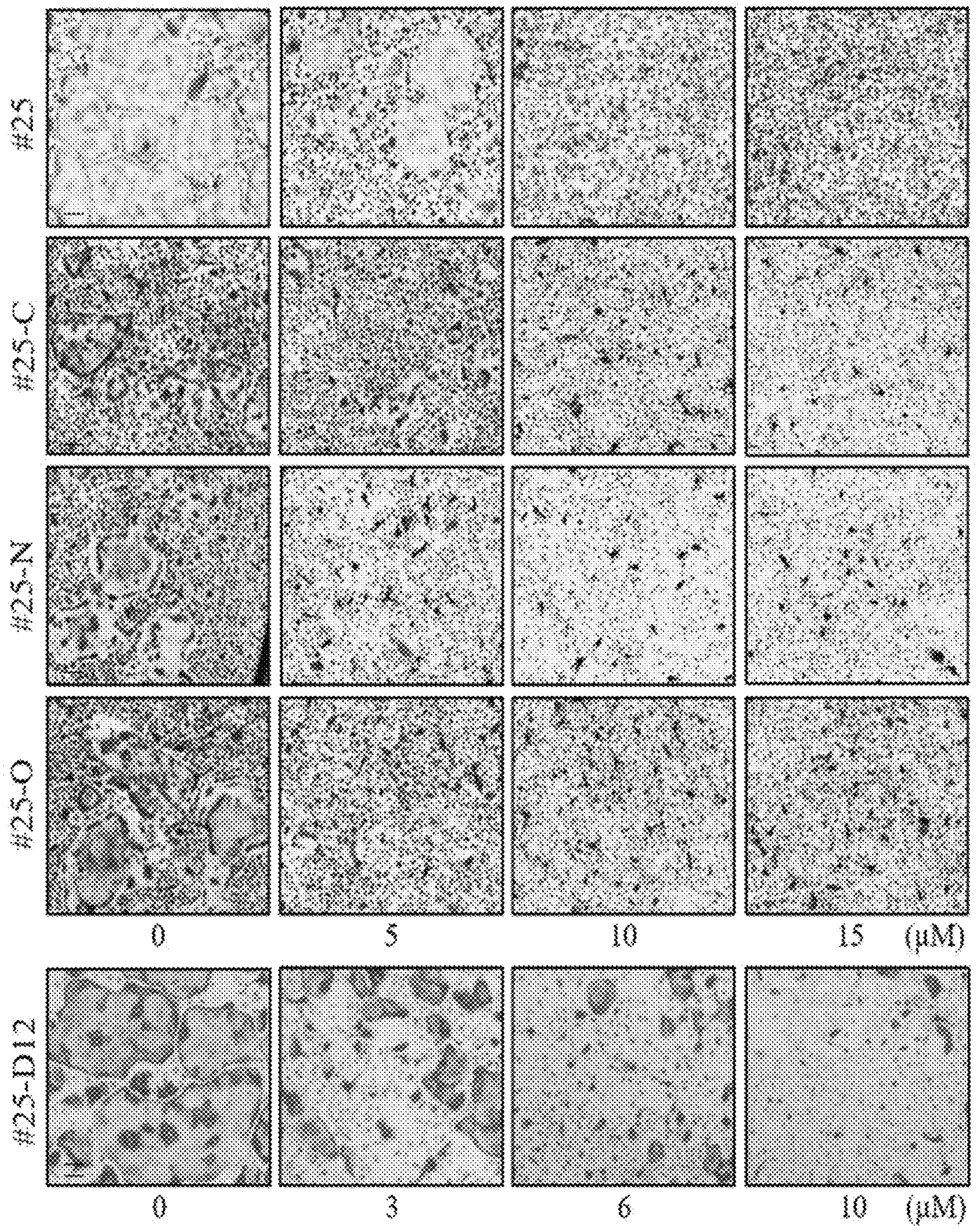
FIG. 2 shows results of confirming differentiated osteoclasts through TRAP staining (*p<0.05, **p<0.01).

2) Confirmation of Osteoclast Differentiation Inhibitory Ability Through TRAP Staining and Assay $1\times10^4$ monocytes isolated from mouse bone marrow were put into a 96-well plate and treated with RANKL and PMSA together to confirm the effect of each PMSA on osteoclast differentiation ability. Each PMSA was used for treatment by concentration. The activity of tartrate-resistant acid phosphatase (TRAP), which has increased expression during osteoclast differentiation, was confirmed using a TRAP activity assay kit (Cosmo Bio, PMC-AK04F-COS) (see FIG. 2). FIG. 2 shows results of confirming the differentiated osteoclasts through TRAP staining (when compared to 0 μM, *<0.05, **p<0.01).

Figure 3:
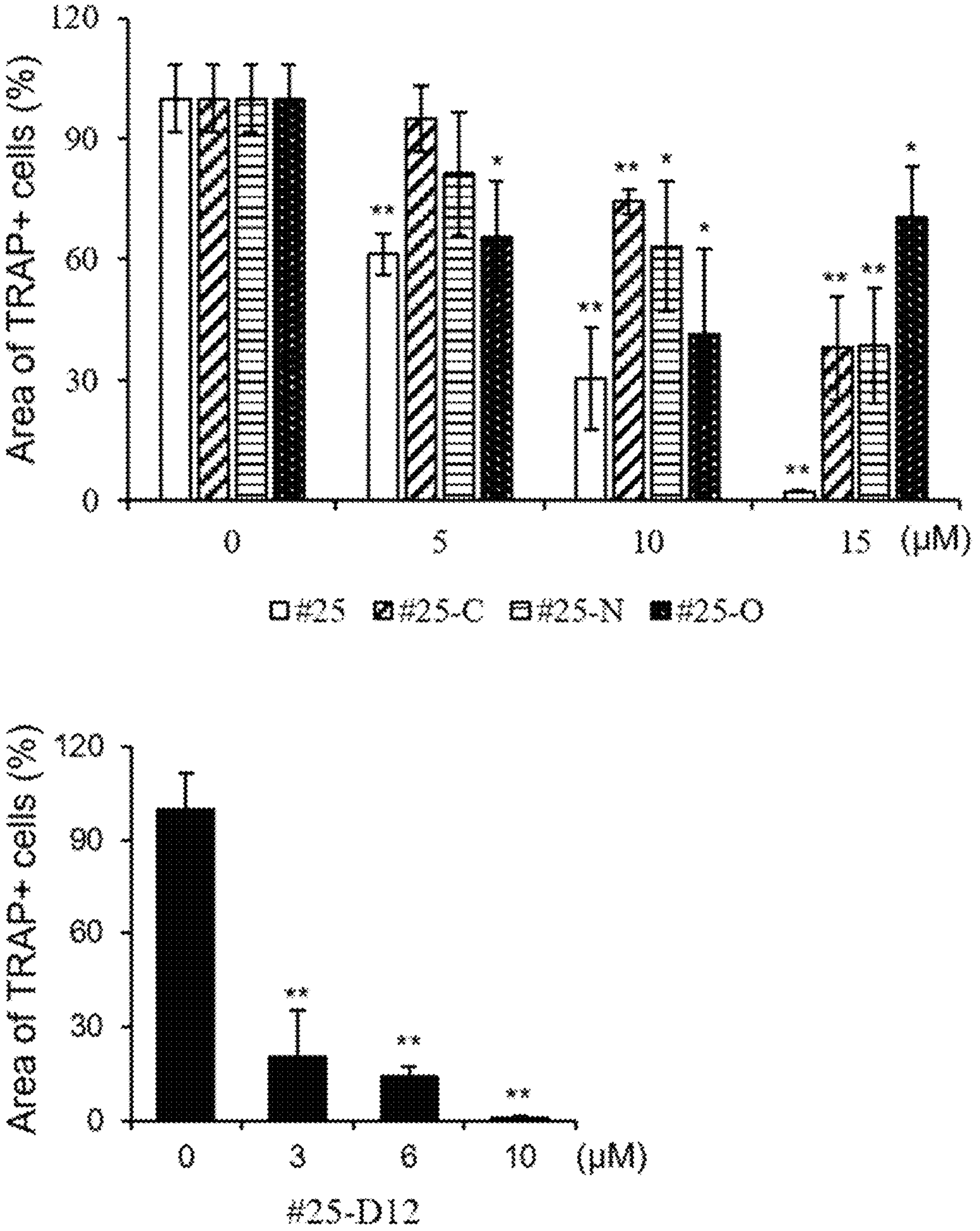
FIG. 3 shows results of confirming the osteoclast differentiation inhibitory ability by calculating an area of differentiated osteoclasts (*p<0.05, **p<0.01).

Further, after staining, the multinuclear cells formed during osteoclast differentiation were observed under a microscope, and each well was photographed and a differentiation area ratio per total area was determined using Image J software. As a result, it was confirmed that each of the PMSA compounds exhibited effective osteoclast differentiation inhibitory ability (see FIG. 3). Specifically, at 10 μM concentration, cells were differentiated into osteoclasts by 30% when using #25 (PMSA-3-Ac), similarly, 74% using #25-C (PMSA-Ph), 63% using #25-N (PMSA-PhN), 41% using #25-PhO (PMSA-O), and only 1% using #25-D12 (PMSA-2-OMe-5-Cl), respectively. FIG. 3 shows results of confirming the osteoclast differentiation inhibitory ability by calculating the area of differentiated osteoclasts (when compared with 0 μM, * p<0.05, ** p<0.01).

2) Assessment of Bone Resorption Inhibition Ability

Figure 4:
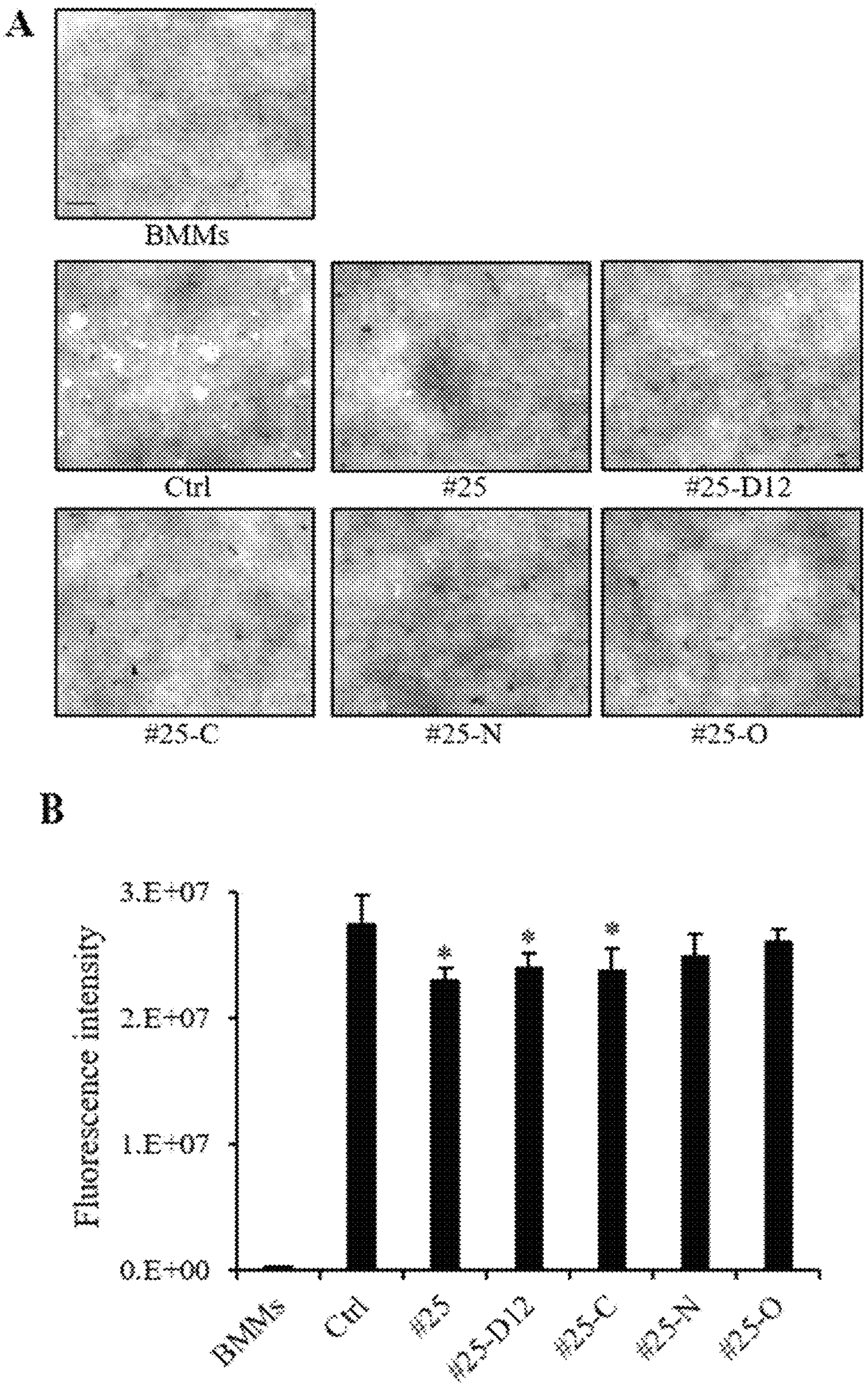
FIG. 4 shows results of confirming the bone resorption ability, wherein A of FIG. 4 shows results of confirming calcium phosphate decomposed by the formation of osteoclasts, while B of FIG. 4 shows results of analyzing the bone resorption ability using fluorescence absorbance.

Bone resorption ability was confirmed using a bone resorption assay kit (Cosmo Rio, CSR-BRA). $2.5\times10^4$ mouse bone marrow cells per well were put into a 48-well plate coated with calcium phosphate, followed by treating the cells with PMSA to perform differentiation for 6 days. After 6 days, a fluorescence absorbance was measured with the culture medium to confirm the bone absorption ability. Further, decomposition degree of calcium phosphate was photographed a microscope to confirm the bone resorption ability. As a result, compared to the differentiated osteoclasts (Ctrl) not treated with PMSA compound, the cells treated with #25 (PMSA-3-Ac), #25-D12 (PMSA-2-OMe-5-Cl) and #25-C (PMSA-Ph) showed decreases in bone resorption ability by 16%, 12.5% and 13.4%, respectively. Further, for the cells treated with #25-N (PMSA-PhN) or #25-O (PMSA-PhO), it could also be confirmed that the bone resorption ability was slightly decreased (see FIG. 4). A of FIG. 4 shows results of confirming calcium phosphate decomposed by the formation of osteoclasts, B of FIG. 4 shows results of analyzing the bone resorption ability using fluorescence absorbance (when compared with Ctrl, *p<0.05, p<0.01). In FIG. 4**, BMMs refer to monocytes that are not differentiated osteoclasts.

Two types of compounds #25 (PMSA-3-Ac) and #25-D12 (PMSA-2-OMe-5-Cl), which were confirmed to be excellent in osteoclast differentiation inhibitory ability in the above analysis results, were used to further implement the following experiment.

3) Confirmation of Decreased Expression of Transcription Factors Related to Osteoclast Differentiation In order to further confirm the inhibitory effect of the PMSA compound on osteoclast differentiation, the intranuclear migration of transcription factors NFATc1 and NF-kB and the expression degree of osteoclast-specific genes regulated by the transcription factors were investigated.

Figure 5:
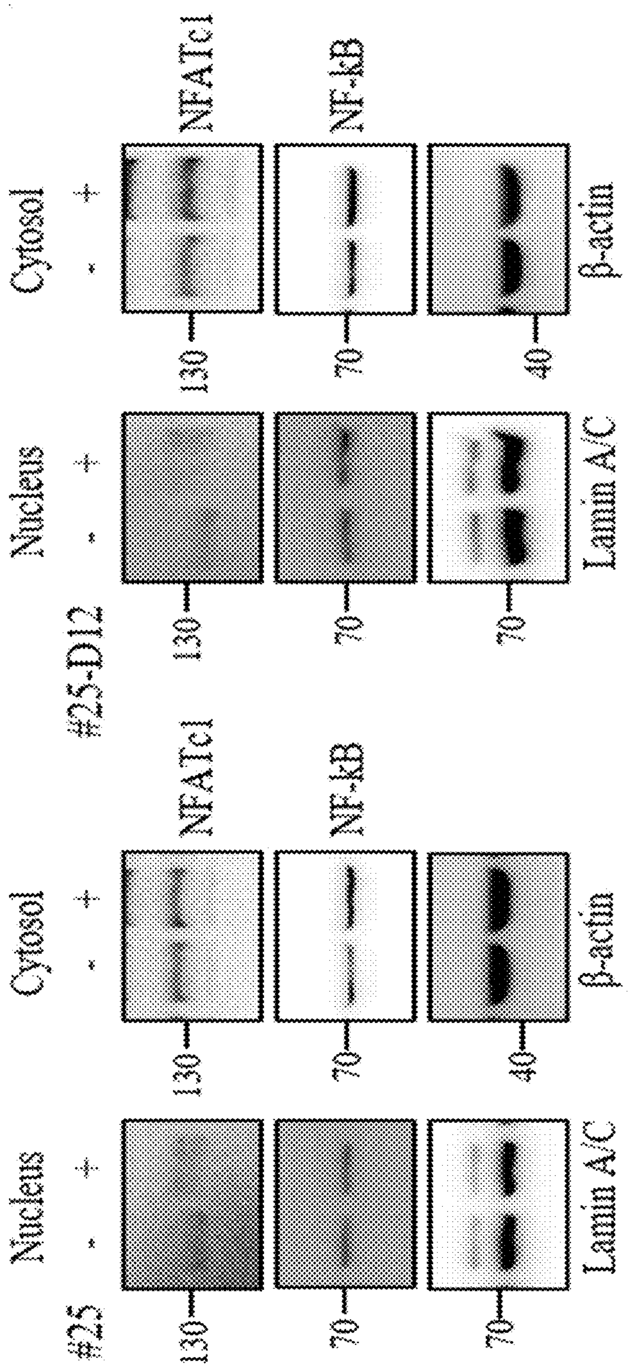
FIG. 5 shows results of confirming the expression of NFATc1 and NF-kB, respectively, in each organelle by means of western blotting after separating the osteoclasts on day 3 of differentiation into nucleus and cytoplasmic proteins

First, in order to confirm the intranuclear migration of transcription factors, osteoclasts differentiated by RANKL for 3 days were separated into nuclear protein and cytoplasmic protein using a NE-PER kit (ThermoFisher scientific 78833). Then, the expression of each of NFATc1 and NF-kB in each organelle was investigated through western blotting. As a result, in the group treated with #25 (PMSA-3-Ac) or #25-D12 (PMSA-2-(Me-5-Cl), NFATc1 was less expressed in the nucleus (see FIG. 5). FIG. 5 shows results of confirming the expression of NFATc1 and NF-kB, respectively, in each organelle by western blotting after isolating osteoclasts on day 3 of differentiation into nuclear and cytoplasmic proteins.

Further, in order to confirm the expression degree of the osteoclast-specific gene, an mRNA expression level was measured by RT-PCR in the PMSA compound-treated cells. RNA was isolated from the cells differentiated into osteoclasts using an RNeasy kit (Qiagen, 74106), quantified using a spectrophotometer, followed by synthesizing 0.5 μg of RNA using reverse transcriptase (Takara, RR037 A). The synthesized cDNA was subjected to qRT-PCR with a QuantStudio 3 real-time PCR system (Applied Biosystems) using Power SYBR Green PCP Master six (Applied Biosystems).

The primers used in qRT-PCR are shown in Table 1 below.

TABLE 1

| Primer name | Sequence | Sequence number |
|---|---|---|
| NFATc1 Forward primer | CCCGTCACATTCTGGTCCAT | SEQ ID NO: 1 |
| NFATc1 Reverse primer | CAAGTAACCGTGTAGCTCCACAA | SEQ ID NO: 2 |
| CatK Forward primer | GGACGCAGCGATGCTAACTAA | SEQ ID NO: 3 |
| CatK Reverse primer | CAGAGAGAAGGGAAGTAGAGTTG TCACT | SEQ ID NO: 4 |
| c-Fos Forward primer | CGAAGGGAACGGAATAAGATG | SEQ ID NO: 5 |
| c-Fos Reverse primer | GCTGCCAAAATAAACTCCAG | SEQ ID NO: 6 |
| DC-STAMP Forward primer | GGGAGTCCTGCACCATATGG | SEQ ID NO: 7 |
| DC-STAMP Reverse primer | AGGCCAGTGCTGACTAGGATGA | SEQ ID NO: 8 |
| OC-STAMP Forward primer | CAGAGTGACCACCTGAACAAACA | SEQ ID NO: 9 |
| OC-STAMP Reverse primer | TGCCTGAGGTCCCTGTGACT | SEQ ID NO: 10 |
| TRAF6 Forward primer | AAAGCGAGAGATTCTTTCCCTG | SEQ ID NO: 11 |
| TRAF6 Reverse primer | ACTGGGGACAATTCACTAGAGC | SEQ ID NO: 12 |

All qPCR experiments were performed in duplicate, and 18S was used as a control. The ddCT method was used for data analysis.

Figure 6:
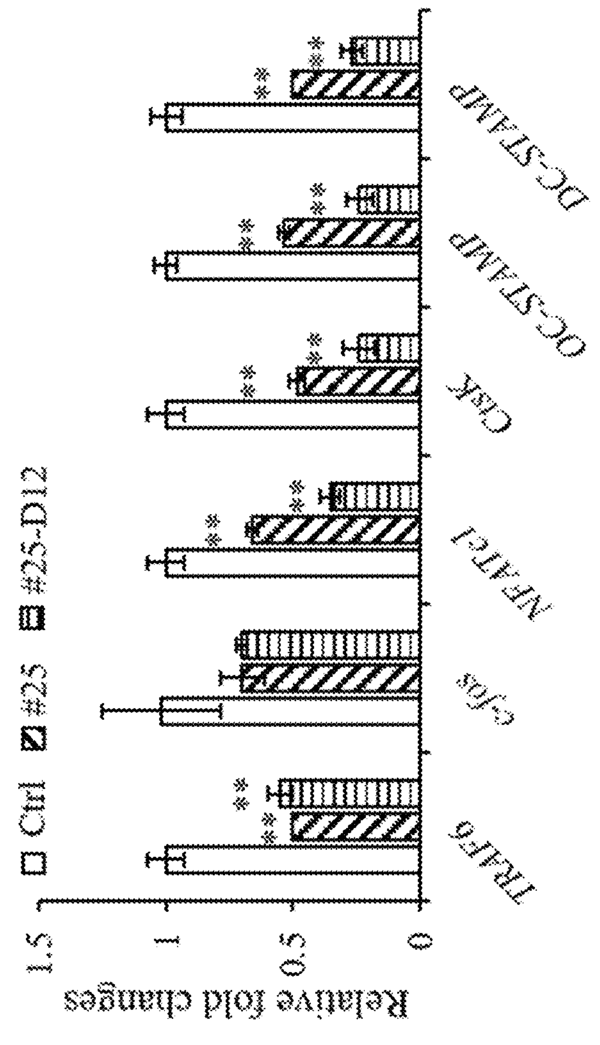
FIG. 6 shows results of confirming the expression of osteoclast-specific genes in osteoclasts on day 3 of differentiation through RT-PCR (**P<0.01).

From RT-PCR results, as compared to the control (Ctrl) without PMSA treatment, the groups treated with #25 (PMSA-3-Ac) or #25-D12 (PMSA-2-OMe-5-Cl) showed decrease in mRNA expression of the osteoclast-specific genes, that is, cathepsin K (CtsK), osteoclast stimulatory transmembrane protein (OC-STAMP) and dendritic cell-specific transmembrane protein (DC-STAMP), respectively (see FIG. 6), FIG. 6 shows results of confirming the expression of an osteoclast-specific gene in osteoclasts on day 3 of differentiation through RT-PGR (compared to the Ctrl control **P<0.01).

Figure 9:
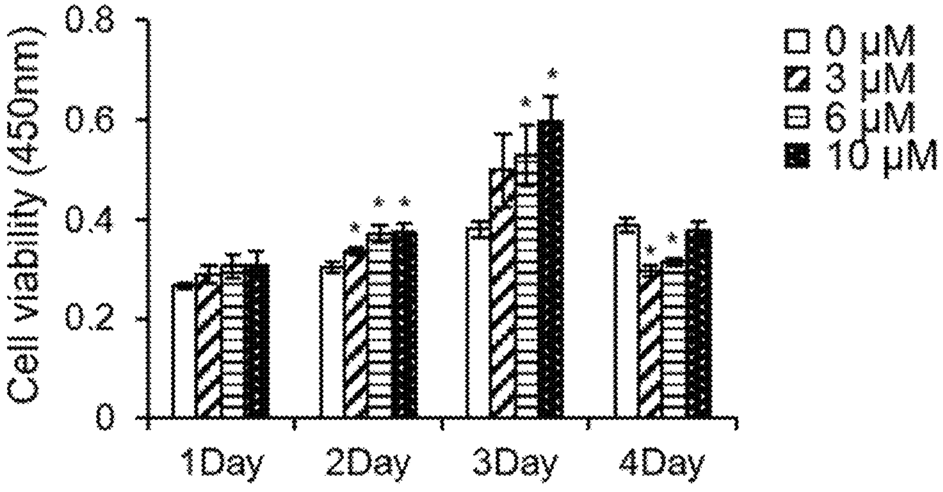
FIG. 9 shows results of evaluating cell viability when mononcytes isolated from mouse bone marrow were treated with the compound represented by Formula 7 by concentration.

From the experimental results, it could be confirmed that #25(PMSA-3-Ac) or #25-D12(PMSA-2-OMe-5-Cl) suppresses the intranuclear migration of NFATc1 as an essential regulator of osteoclast differentiation, as well as a regulatory mechanism of normal osteoclast differentiation, thereby inhibiting the expression osteoclast-specific genes and, consequently, inhibiting the differentiation of osteoclasts 2. Inhibitory Effects of the Compound Represented by Formula 7 on Osteoclast Differentiation 1) MTT Assay for Cytotoxicity Evaluation $1\times10^4$ monocytes isolated from mouse bone marrow per well were put into a 96-well plate, and in order to assess cell viability, the cells were cultured for 4 days while being treated with PSTP-3,5-Me at different concentrations (3-10 μM). A cell viability assay reagent (DoGen, EZ-3000) was used for treatment with 1/10 of the volume of the medium, and the cells were cultured at 37° C. for 30 minutes and confirmed at 450 nM. As a result, it was confirmed that the compound represented by Formula 7 did not affect cell viability (see FIG. 9). In other words, it is understood that no cytotoxicity appeared.

2) Isolation of Mouse Bone Marrow Cells and Differentiation of Osteoclasts

The bone marrow of a 12-week-old female mouse was isolated from the hip bone, femur and tibia, and then cultured in α-MEM medium (Gibco, 12561-056, 10% fetal bovine serum, 1% penicillin/streptomycin) containing macrophage colony stimulating factor (M-CSF, PeproTech, cat, #315-02, 30 ng/ml) for 3 days to isolate only monocytes. The isolated monocytes were treated with RANKL (PeproTech, cat #315-11, 50 ng/ml) to induce osteoclast differentiation. Further, PSTP-3,5-Me was also used for treatment, followed by culturing the cells for 3 or 5 days.

3) TRAP Staining and Assay for Analysis of Osteoclast Differentiation Inhibitory Ability $1\times10^4$ monocytes isolated from mouse bone marrow were nut into a 96 well-plate and treated with RANKL to confirm the effect pf PSTP-3,5-Me on osteoclast differentiation ability. The activity of tartrate-resistant acid phosphatase (TRAP), which has increased expression during osteoclast differentiation, was confirmed using a TRAP activity assay kit (Cosmo Bio, PMC-AK04F-COS), which is shown in A of FIG. 10.

Figure 10:
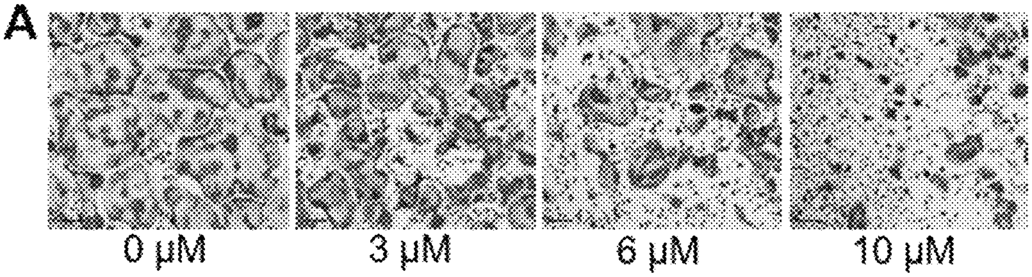
FIG. 10 shows results of confirming effects on the osteoclast differentiation ability using a tartrate-resistant acid phosphatase (TRAP) activity assay kit (Sigma-Aldrich, 387A-1kt) when monocytes isolated from the mouse bone marrow were treated with the compound of the present invention together with RANKL.
Figure 10:
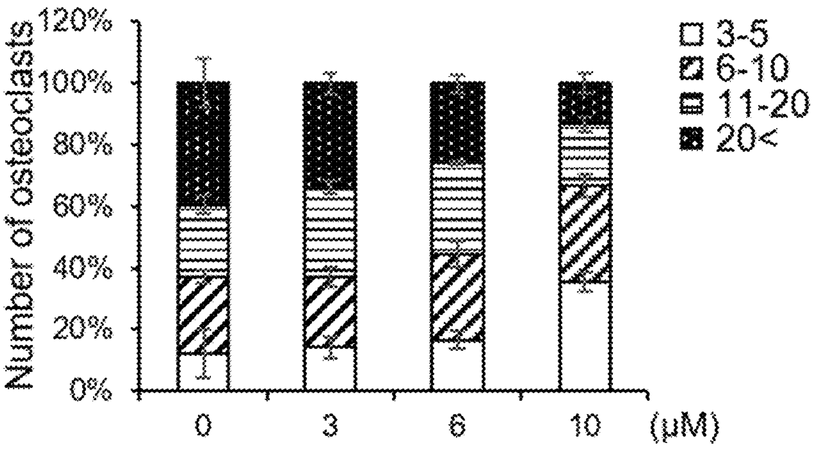

Further, osteoclasts having 3-5, 6-10, 11-20, and 21 or more cell nuclei contained in differentiated osteoclasts were classified and shown in B of FIG. 10.

As compared to the group in which osteoclasts are normally differentiated, the group treated with the compound represented by Formula 7 showed significant reduction in the differentiation area, the number of osteoclasts and giant multinuclear cells. From this result, it could be confirmed that the compound of the present invention has osteoclast differentiation inhibitory ability.

4) Confirmation of Osteoclast Differentiation Inhibitory Ability by Reducing the Expression of CatK and NFATc1 Genes In order to further confirm the inhibitory effect of PSTP-3,5-Me on osteoclast differentiation, the expression levels genes related to osteoclast production were investigated. mRNA expression of specific markers associated with osteoclast production was measured by RT-PCR in 0 or 6 μM PSTP-3,5-Me-treated cells.

For qRT-PCR, total RNA was extracted from BMMs using a TRIzol reagent (Thermo Fisher Scientific, MA, USA). Complementary DNA was synthesized from the total RNA using a Verso cDNA synthesis kit (Thermo Fisher Scientific, MA, USA). Thereafter, quantitative PCR (qPCR) was performed using the QuantStudio 3 real-time PCR system (Applied Biosystems, CA, USA) together with Power SYBR Green PCR Master Mm (Applied Biosystems, CA, USA).

The primers used in the qRT-PCR are shown in Table 2 below.

TABLE 2

| Primer name | Sequence | Sequence number |
|---|---|---|
| NFATc1 Forward primer | CCCGTCACATTCTGGTCCAT | SEQ ID NO: 1 |
| NFATc1 Reverse primer | CAAGTAACCGTGTAGCTCCACAA | SEQ ID NO: 2 |
| CatK Forward primer | GGACGCAGCGATGCTAACTAA | SEQ ID NO: 3 |
| CatK Reverse primer | CAGAGAGAAGGGAAGTAGAGTTGTCACT | SEQ ID NO: 4 |
| c-Fos Forward primer | CGAAGGGAACGGAATAAGATG | SEQ ID NO: 5 |
| c-Fos Reverse primer | GCTGCCAAAATAAACTCCAG | SEQ ID NO: 6 |
| DC-STAMP Forward primer | GGGAGTCCTGCACCATATGG | SEQ ID NO: 7 |
| DC-STAMP Reverse primer | AGGCCAGTGCTGACTAGGATGA | SEQ ID NO: 8 |
| OC-STAMP Forward primer | CAGAGTGACCACCTGAACAAACA | SEQ ID NO: 9 |
| OC-STAMP Reverse primer | TGCCTGAGGTCCCTGTGACT | SEQ ID NO: 10 |
| Acp5 Forward primer | CAGCTGTCCTGGCTCAAAA | SEQ ID NO: 13 |
| Acp5 Reverse primer | ACATAGCCCACACCGTTCTC | SEQ ID NO: 14 |

All qPCR experiments were performed in duplicate, and 18S was used as a control. The ddCT method was used for data analysis.

Figure 11:
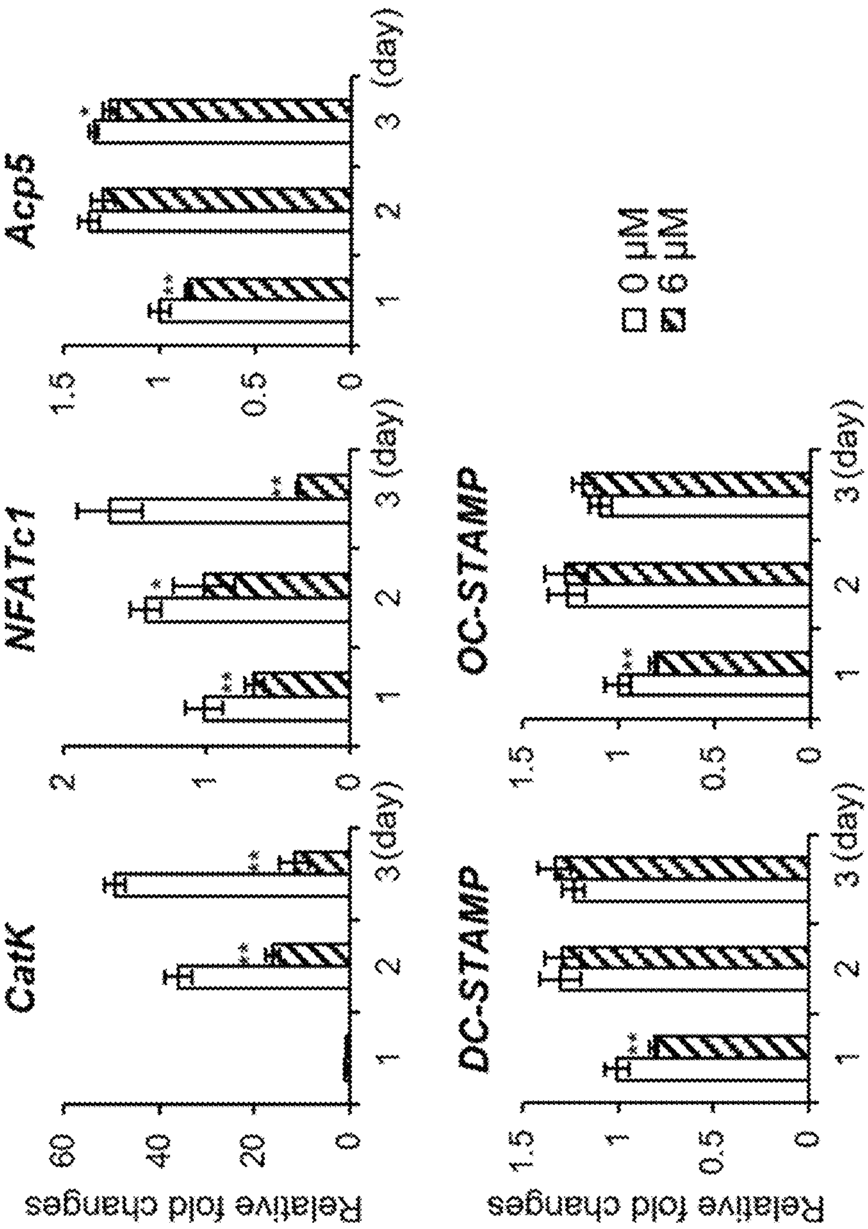
FIG. 11 shows results of confirming mRNA expression levels of CatK and NFATc1, respectively.

As a result of qRT-PCR as shown in FIG. 11, the expression degree of each of CatK and NFATc1 in the osteoclast formation process was significantly decreased during osteoclast differentiation by PSTP-3,5-Me (6 μM), as compared to the control (0 μM). Acp5 expression level was slightly decreased compared to the control, while DC-STAMP and OC-STAMP expression levels were decreased on day 1.

Figure 12:
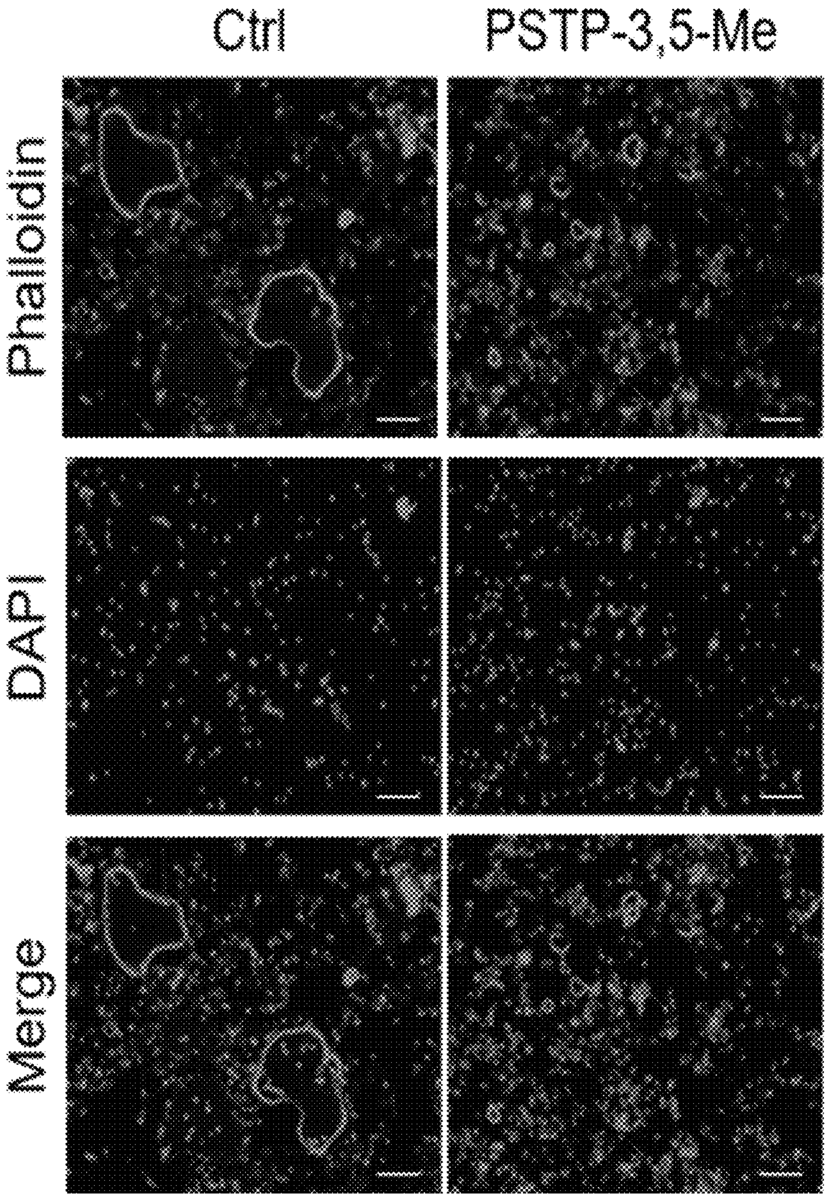
FIG. 12 shows results of confirming the ability of differentiation into multinuclear cells to the extent of F-actin formation.

5) Confirmation of Actin-Ring Formation Inhibition and Bone Resorption Inhibitory Effect In order to determine the activity of differentiated osteoclasts, an ability to differentiate the cells into multinuclear cells was firstly confirmed through F-actin staining. Specifically, $5\times10^4$ mouse hone marrow cells per well were put into a 24-well plate in which glass coated with L-Lysine was placed (Corning, 354085). Simultaneously, the cells were treated with PSTP-3,5-Me 6 uM and cultured for 4 to 5 days. The differentiated cells were fixed with 4% formaldehyde for 10 minutes and washed with PBS. For the antigen-antibody reaction, a reaction was conducted in 0.1% Triton-PBS for 20 minutes, followed by reacting the same in 1% BSA for 1 hour. Thereafter, the F-actin antibody (Thermo Fisher Scientific, A12379) was reacted for 1 hour and than washed. Cell nuclei were stained through 4',6-diamidino-2-phenylindole (DAPI, Dilactate, Thermo Fisher Scientific, D3571) staining, and then photographed under a microscope. As a result, it was confirmed by comparing shies of F-actin that PSTP-3,5-Me inhibited differentiation into multinuclear cells. Ae a result, as shown in FIG. 12, a small-sized actin-ring structure was detected in the presence of PSTP-3,5-Me, whereas the cells in the control showed a unique actin-ring formation.

Further, the bone resorption ability was confirmed using a bone resorption assay kit (Cosmo Bio, CSR-BRA). $2.5\times10^4$ mouse bone marrow cells per well were put into a 48-well plate coated with calcium phosphate, and were differentiated for 6 days while being treated with PSTP-3,5-Me. After 6 days, the fluorescence absorbance was measured with the culture medium to confirm the bone absorption ability.

Figure 13:
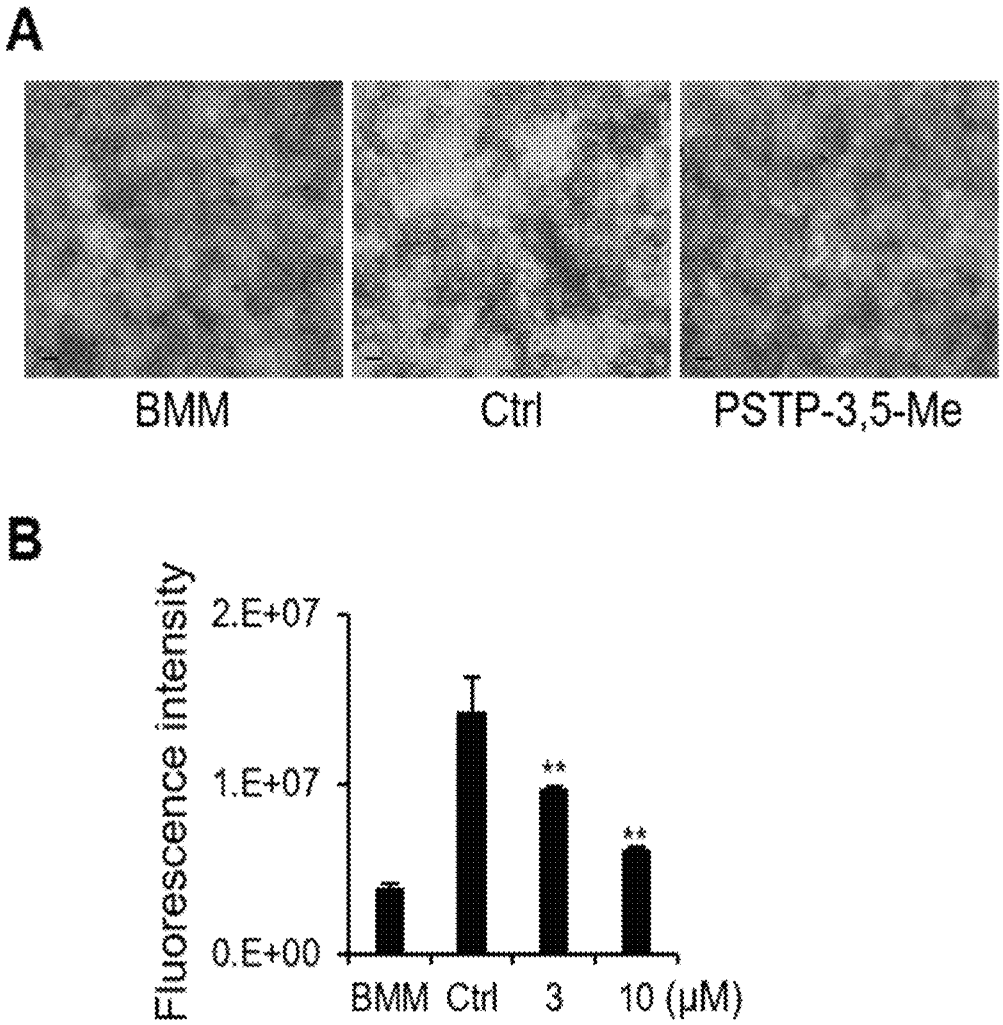
FIG. 13 shows results of confirming the bone resorption ability of osteoclasts.

A of FIG. 13 shows the visualization of the bone resorption region using an optical microscope, and the bone resorption region was not largely shown upon treatment with PSTP-3,5-Me. B of FIG. 13 shows fluorescence intensity in the presence of: RANKL; and 0, 3 or 10 μM of PSTP-3,5-Me. As shown in B of FIG. 13, the bone resorption ability was significantly decreased in a dose-dependent manner by PSTP-3,5-Me.

From the above results, it can be confirmed that PSTP-3,5-Me inhibits the reduction of bone resorption activity.

Confirmation of Osteoblast Differentiation Effects

1. Confirmation of Osteoblast Differentiation Effects of Compounds Represented by Formulae 2 to 6

After collecting cells from C57BL/6J mouse calvaria at the age of 3 days, the cells were seeded on a 96-well plate in an amount of $4\times10^3$ cells per well, and then treated with 100 ng/ml of hBMP2 as a differentiation inducer. Simultaneously, the cells were treated with the compound of the present invention and cultured for 7 days, followed by ALP staining to assess differentiation influence. Specific experimental methods and results are as follows.

1) Isolation of Mouse Skull Cells and Differentiation of Osteoblasts

Precursor cells isolated from the mouse skull were treated with hBMP2 (Bone morphogenic protein 2, Sino biological, 10426-HNAE, 100 ng/ml) to induce differentiation into osteoblasts. Differentiated osteoblasts could be discriminated through alkaline phosphatase (ALP) staining as an osteoblast-specific protein. When the progenitor cells were treated with hBMP2, each of the 35D35 compounds was also used for treatment, followed by culturing the cells for 7 days while changing the medium every 2 to 3 days.

2) ALP (Alkaine Phosphatase) Staining for Analysis of Osteoblast Differentiation Ability $4\times10^3$ osteoblast progenitor cells were put into a 96-well plate and treated with hBMP2 to induce differentiation of osteoblasts. At this time, the cells were treated with #25 (PMSA-3-Ac) and #25-D12 (PMSA-2-OMe-5-Cl), respectively, and then cultured for 7 days.

For the analysis of osteoblast differentiation ability, the medium was discarded 7 days after induction of differentiation to confirm the activity of ALP, which shows increased expression in the early stage of osteoblast differentiation, the remaining product was washed once with a Hanks' Balanced Salt Solution (HBSS, welgene) and put into 70% cold ethanol, followed by fixing the cells for 1 hour. After discarding the ethanol, the remaining product was washed with HBSS, followed by adding a NBT solution (Sigma, B1911) in an amount of 100 μl per well and staining for 15 minutes. By washing twice with water, the remaining dye was eliminated. After ALP staining, a degree of color development was measured using Image J software, and then graphed for comparison. As a result, it was confirmed that #25 (PMSA-3-Ac) and #25-D12 (PMSA-2-OMe-5-Cl) did not inhibit or activate osteoblast differentiation (see FIG. 7). In other words, it can be seen that the differentiation of osteoblasts is not affected by treatment with the PMSA compound.

Figure 7:
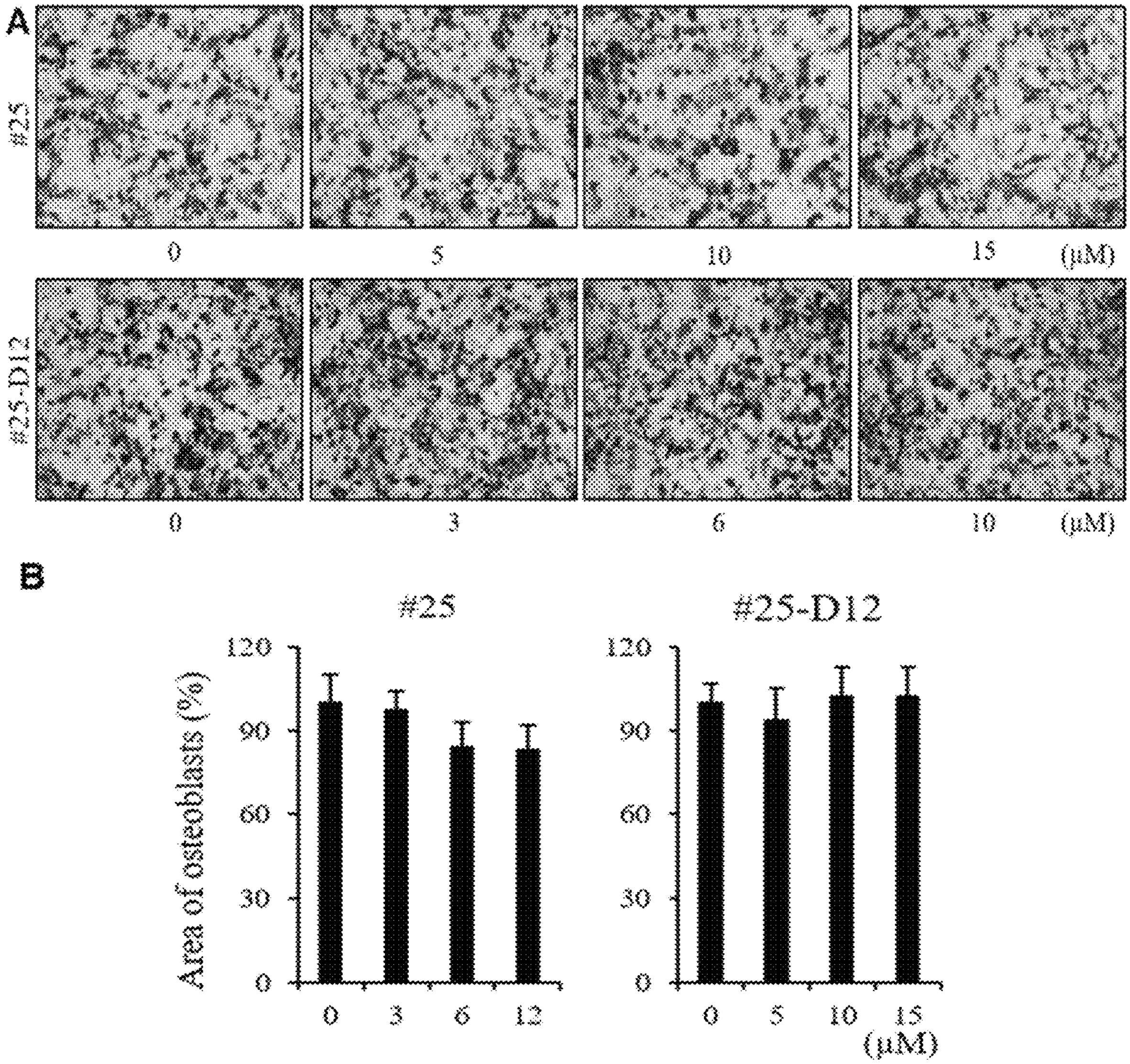
FIG. 7 shows results of confirming the osteoblast differentiation ability by a PMSA compound through ALP staining

FIG. 7 shows results of confirming the osteoblast differentiation ability by the PMSA compound through. ALP staining. Specifically, A of FIG. 7 shows results of confirming the differentiated osteoblasts through ALP staining (scale bar=100 μm), while B of FIG. 7 shows results of confirming the differentiation ability calculating an area of the stained osteoblast.

2. Confirmation of Osteoblast Differentiation Effects of Compound Represented by Formula 7

1) Isolation of Mouse Skull Cells and Differentiation of Osteoblasts

Precursor cells isolated from the mouse skull were treated with hBMP2 (Bone morphogenic protein 2, Sino biological, 10426-HNAE) to induce differentiation into osteoblasts. At this time, PSTP-3,5-Me was also used for treatment, followed by culturing the cells or 7 days while changing the medium every 2 to 3 days.

2) ALP Staining for Analysis of Osteoblast Differentiation Ability $4\times10^3$ osteoblast progenitor cells were put into a 96-well plate and treated with hBMP2 to induce differentiation of osteoblasts. At this time, PSTP-3,5-Me was also used for treatment, followed by culturing the cells for 7 days. For the analysis of osteoblast differentiation ability, the medium was discarded 7 days after induction of differentiation to confirm the activity of alkaine phosphatase (ALP), which shows increased expression in the early stage of osteoblast differentiation, the remaining product was washed once with a Hanks' Balanced Salt Solution (HBSS, welgene) and put into 70% cold ethanol, followed by fixing the cells for 1 hour. After discarding the ethanol, the remaining product was washed with HBSS, followed by adding a NBT solution (Sigma, B1911) in an amount of 100 μl per well and staining for 15 minutes.

Figure 14:
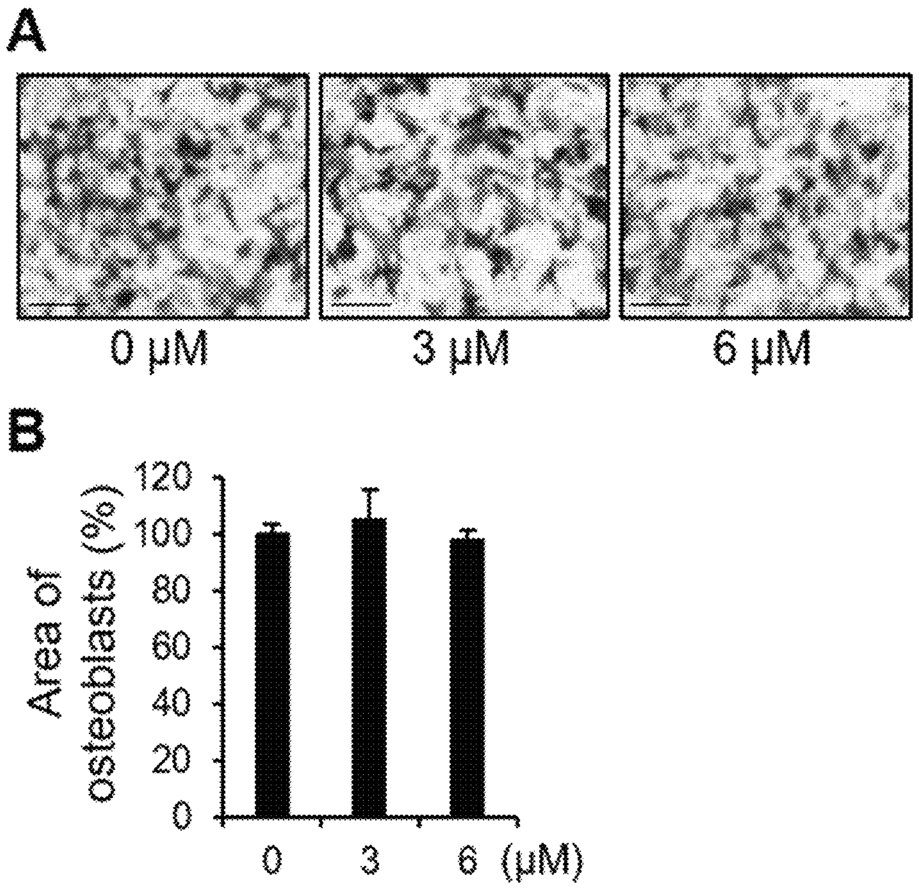
FIG. 14 shows results of confirming the differentiation ability of osteoblasts upon treatment with the compound represented by Formula 7.

After ALP staining, the degree of color development was measured using Image J software, and then graphed for comparison. The results are shown in FIG. 14. Referring to FIG. 14, it can be confirmed that the differentiation of osteoblasts is not affected by the treatment of PSTP-3,5-Me.

Confirmation of In Vivo Effects of PSMA Compound

In order to confirm in vivo efficacy of the PMSA compound, an ovariectomized animal model (OVX, ovariectomized mouse) with osteoporosis due to estrogen deficiency after ovariectomy in 8-week-old female mouse was prepared. #25 (PMSA-3-Ac, 25 mg/kg) or #25-D12 (PMSA-2-OMe-5-Cl, 20 mg/kg) were injected intraperitoneally once every two days to the ovariectomized mouse model. After 4 weeks, the tibia of the mouse was analyzed for bone density by microcomputer tomography.

As a result, it was observed that the OVX model injected with #25-D12 (PMSA-2-OMe-5-Cl) exhibited higher bone density and bone volume than the control (OVX). Specifically, #25-D12 (PMSA-OMe-5-Cl) treatment group exhibited a total bone volume (TV) increased by 5.4%, bone volume (BV) increased by 6.9%, trabecular volume (Th.V) increased by 2.7 times, cortical volume (Ct.V) increased by 5.4%, and trabecular bone mineral density (Th. BMD) increased by 42.3%, as compared to the control (see FIG. 8). In particular, it was confirmed that treatment with #25-D12 had effects of preventing bone loss in the trabecular bone portion.

Figure 8:
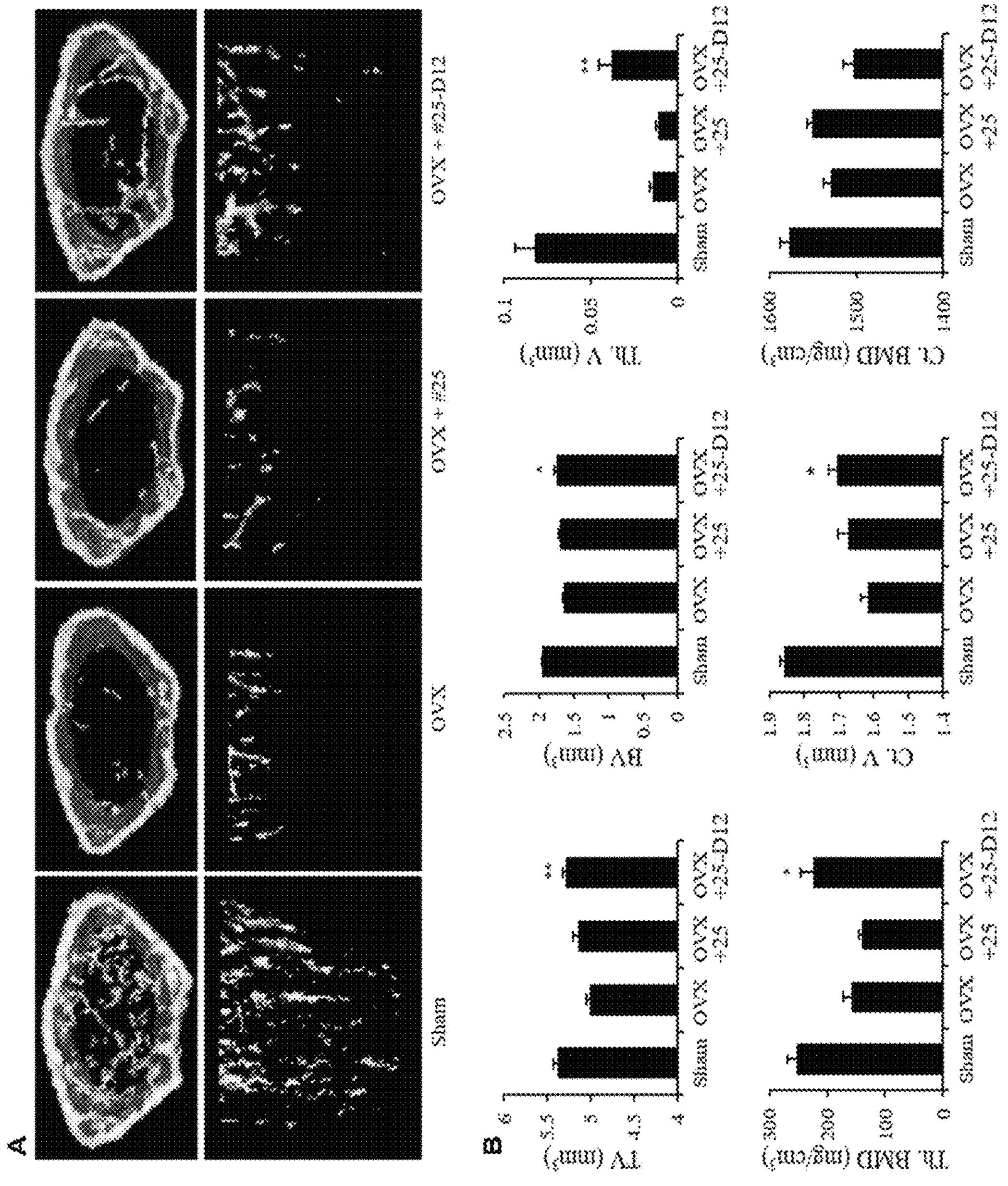
FIG. 8 shows results of verifying in vivo effects of the PMSA compound in OVX mice.

FIG. 8 shows results of verifying in vivo effects of the PMSA compound in OVX mice. Specifically, A of FIG. 8 shows results of microcomputerized tomography of the tibia of a mouse model (Sham: a control in which the ovaries are not removed), while B of FIG. 8 shows a graph for analysis of the microcomputerized tomography results (TV: total bone volume, BV: bone volume, Th. V: trabecular volume, Th. BMD: trabecular bone mineral density, Ct. V: cortical volume, Ct. BMD: cortical bone mineral density).

Absorption, Distribution, Metabolism and Excretion (ADME) Test of PMSA Compounds In order to analyze the drug metabolism of PMSA compound, ADME evaluation was requested to the Daegu-Gyeongbuk Advanced Medical industry Promotion Foundation (DGMIF). Metabolic stability of drugs using liver microsomes (microsomal stability), drug metabolism inhibitory ability by five CYP450 enzymes, plasma metabolism (plasma stability), plasma protein binding, and intestinal permeability of drugs (PAMPA, parallel artificial membrane permeability assay) were analyzed. As a result, the PMSA compounds of the present in (#25, #25-12, #25-C, #25-N, and #25-O) showed low toxicity and good with plasma proteins, thereby making it easy to move in the blood. Further, it was confirmed that the permeability resistance was excellent (see Table 3 below). On the other hand, for one of PMSA derivatives, that is, 2-(N-(3,5-dimethylphenyl) methylsulfinamido)-N-(2 (phenylthio)phenyl)propanamide (#25-D5), intestinal permeability of the drug (PAMPA) was not measured. Further, it was confirmed that utility as a drug such as influence on activity of CYP3A4 was not higher than other derivatives (see Table 3 below).

TABLE 3

| | Microsomal stability (>60%) | CYP (remaining activity >50%) | | | | | Plasma S Human 30 min/120 min | PPB Human | PAMPA (>40) $Pe(10^{-6}$ |
|---|---|---|---|---|---|---|---|---|---|
| | H/M (%) | 1A2 | 2C9 | 2C19 | 2D6 | 3A4 | (% Remaining) | (%, bound) | cm/sec) |
| #25 | 8.7/8.0 | 85.7 | 63.7 | 6.2 | 80.4 | 53.3 | 87.1/97.3 | 98.4 | 59.4 ± 1.6 |
| #25-D12 | 13.9/21.7 | 77.9 | 59.8 | 6.3 | 85.5 | 26 | 98.3/97.8 | 99.8 | 49 ± 2 |
| #25-C | 50.6/3.7 | 96.8 | 67.2 | 6.9 | 18.3 | 72 | 100/100 | 97.9 | 76.64 |
| #25-N | 3.3/4.0 | 81.6 | 47 | 9 | 12.6 | 43.1 | 100/100 | 97.9 | 47.2 |
| #25-O | 12.5/3.1 | 100 | 49.7 | 10.4 | 53.1 | 70.1 | 94.3/96.4 | 98.4 | 66.18 |
| #25-D5 | 10.9/14.7 | 85.1 | 52.4 | 21.7 | 87.3 | 13.4 | 100/100 | 99.8 | ND |

From the above-described experimental results, it was confirmed that the PMSA compound exhibited excellent osteoclast differentiation inhibitory effects upon 10 μM treatment, and did not affect osteoblast differentiation. Further, according to molecular biological experiments, it was confirmed that the PMSA compound inhibits the expression of osteoclast related genes by preventing intranuclear migration of NFATc1. In particular, #25-D12 (PMSA-2-OMe-5-Cl) effectively reduced bone loss in vivo even in the OVX mouse model. In addition, according to analysis of drug metabolism, it was confirmed that PMSA compounds could be developed as drugs due to their low toxicity. Therefore, it is believed that the compounds of the present invention may function as an effective bone metabolism inhibitor.

A sequence listing electronically submitted with the present application on Jan. 18, 2022 as an ASCII text file named 20220118_Q72722LC04_TU_SEQ, created on Jan. 18, 2022 and having a size of 3000 bytes, is incorporated herein by reference in its entirety.

What is claimed is:

1. A composition comprising a compound represented by Formula 1 below, or a pharmaceutically acceptable salt thereof:

[Formula 1]

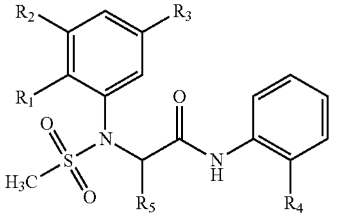

wherein $R_1$ is H or C1 to C3 alkoxy;

$R_2$ and $R_3$ are each independently H, C1 to C3 alkyl, C1 to C3 acyl or halo;

$R_4$ is phenyl, phenoxy or phenylamino; and $R_5$ is H or C1 to C3 alkyl, and with the proviso that, when $R_4$ is phenoxy and $R_1$ is H, $R_2$ and $R_3$ are each not C1 to C3 alkyl.

2. The composition according to claim 1, wherein $R_1$ is H or methoxy; $R_2$ and $R_3$ are each independently H, methyl, acetyl or chloro; and $R_5$ is H or methyl.

3. A composition comprising a compound represented by Formula 1 below, or a pharmaceutically acceptable salt thereof:

[Formula 1]

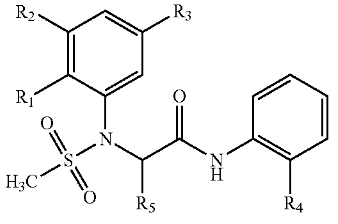

wherein $R_1$ is C1 to C3 alkoxy, $R_2$ is H, C1 to C3 alkyl, C1 to C3 acyl or halo, $R_3$ is halo, $R_4$ is phenyl, phenylthio, phenoxy or phenylamino, and $R_5$ is H;

$R_1$, $R_3$ and $R_5$ are H, $R_4$ is phenyl, phenoxy or phenylamino, and $R_2$ is C1 to C3 acyl; or $R_1$ is H, $R_4$ is phenyl, phenoxy or phenylamino, and $R_2$, $R_3$ and $R_5$ are methyl.

4. The composition according to claim 1, wherein the compound represented by Formula 1 above is selected from the group consisting of N-([1,1'-biphenyl]-2-yl)-2-(N-(3-acetylphenyl)methylsulfonamido)acetamide), 2-(N-(3-acetylphenyl)methylsulfonamido)-N-(2-(phenylamino)phenyl)acetamide, and 2-(N-(3-acetylphenyl)methylsulfonamido)-N-(2-phenoxyphenyl)acetamide.

5. A method for treating a bone disease, the method comprising administering to a subject having the bone disease a composition comprising an effective amount of a compound represented by Formula 1 below, or a pharmaceutically acceptable salt thereof:

[Formula 1]

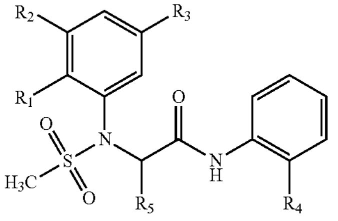

wherein $R_1$ is H or C1 to C3 alkoxy;

$R_2$ and $R_3$ are each independently H, C1 to C3 alkyl, C1 to C3 acyl or halo;

$R_4$ is phenyl, phenylthio, phenoxy or phenylamino; and $R_5$ is H or C1 to C3 alkyl, wherein the bone disease is at least one selected from the group consisting of osteoporosis, rheumatoid arthritis, periodontitis, Paget's disease, osteomalacia, osteopenia, bone atrophy, and osteoarthritis.

6. The method of claim 5, wherein $R_1$ is H or methoxy; $R_2$ and $R_3$ are each independently H, methyl, acetyl or chloro; and $R_5$ is H or methyl.

7. The method of claim 5, wherein $R_1$ is C1 to C3 alkoxy, $R_3$ is halo, and $R_5$ is H;

$R_1$, $R_3$ and $R_5$ are H, and $R_2$ is C1 to C3 acyl; or $R_1$ is H, and $R_2$, $R_3$ and $R_5$ are methyl.

8. The method of claim 5, wherein the compound represented by Formula 1 above is selected from the group consisting of: 2-(N-(3-acetylphenyl)methylsulfonamido)-N-(2-(phenylthio)phenyl)acetamide; 2-(N-(5-chloro-2-methoxyphenyl)methylsulfonamido)-N-(2-(phenylthio)phenyl)acetamide; N-([1,1'-biphenyl]-2-yl)-2-(N-(3-acetylphenyl)methylsulfonamido)acetamide); 2-(N-(3-acetylphenyl)methylsulfonamido)-N-(2-(phenylamino)phenyl)acetamide; 2-(N-(3-acetylphenyl)methylsulfonamido)-N-(2-phenoxyphenyl)acetamide; and N2-(3,5-dimethylphenyl)-N2-(methylsulfonyl)-N-[2-(phenylthio)phenyl]alanineamide.

* * * * *